(12) United States Patent
Vunjak-Novakovic et al.

(10) Patent No.: US 9,888,680 B2
(45) Date of Patent: Feb. 13, 2018

(54) FUNCTIONAL RECOVERY OF HUMAN LUNGS FOR TRANSPLANTATION

(71) Applicant: The Trustees of Columbia University in the City of New York, New York, NY (US)

(72) Inventors: Gordana Vunjak-Novakovic, New York, NY (US); Joshua Sonett, Ho Ho Kus, NJ (US); John O'Neill, New York, NY (US); Matthew Bacchetta, New York, NY (US); Donald O. Freytes, Summit, NJ (US); Gopal Singh, New York, NY (US); Scott A. Kanner, Brooklyn, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 14/245,387

(22) Filed: Apr. 4, 2014

(65) Prior Publication Data
US 2014/0322696 A1  Oct. 30, 2014

Related U.S. Application Data

(60) Provisional application No. 61/808,621, filed on Apr. 4, 2013, provisional application No. 61/920,117, filed on Dec. 23, 2013.

(51) Int. Cl.
*A01N 1/00* (2006.01)
*A01N 1/02* (2006.01)

(52) U.S. Cl.
CPC ......... *A01N 1/0247* (2013.01); *A01N 1/0226* (2013.01)

(58) Field of Classification Search
CPC ................... A61M 16/0463; C12M 21/08
See application file for complete search history.

(56) References Cited

U.S. PATENT DOCUMENTS

| | | | |
|---|---|---|---|
| 5,776,747 A | 7/1998 | Aebischer | |
| 5,968,008 A * | 10/1999 | Grams | A61M 1/0084 604/264 |
| 6,013,048 A * | 1/2000 | Podany | A61B 8/546 604/22 |
| 2004/0029096 A1* | 2/2004 | Steen | A01N 1/02 435/1.1 |
| 2009/0202977 A1* | 8/2009 | Ott | C12N 5/0657 435/1.2 |
| 2010/0158877 A1 | 6/2010 | Hamilton | |

(Continued)

OTHER PUBLICATIONS

Petersen et al. "Tissue-Engineered Lungs for in Vivo Implantation." Science, vol. 329 (Jul. 30, 2010), pp. 538-541.*

(Continued)

*Primary Examiner* — William H Beisner
(74) *Attorney, Agent, or Firm* — Lisa A. Chiarini; Matthew S. Gibson; Reed Smith LLP

(57) ABSTRACT

The vasculature of a donor lung is perfused with a lung preserving fluid to preserve its structure. At the same time, a decellularization fluid is perfused through the airways, which strips away donor cells. The decellularized region is then seeded with pulmonary cells of the transplant recipient, which regenerate the lung. The pulmonary cells may be derived from stem cells, and the decellularization can be targeted to reduce the quantity of cells required.

16 Claims, 30 Drawing Sheets

(56) References Cited

U.S. PATENT DOCUMENTS

2011/0045045 A1    2/2011  Cortiella
2012/0064050 A1    3/2012  Calle
2012/0141439 A1    6/2012  Ott
2012/0183944 A1    7/2012  Taylor

OTHER PUBLICATIONS

D Currow, A Ward, K Clark, CM Burns, AP Abernethy. Caregivers for people with end-stage lung disease: "Characteristics and unmet needs in the whole population." Int J Chron Obstruct Pulmon Dis., vol. 3., Issue 4., pp. 753-762. 2008.
B Parizkova, IG Wright. "Cardiopulmonary transplantation." Anesth Inten Med., vol. 13., Issue 10., pp. 499-502., 2012.
K Takahashi, S Yamanaka. "Introduction of Pluripotent Stem Cells from Mouse Embryonic and Adult Fibroblast Cultures by Defined Factors." Cell, vol. 126, Isue 4., pp. 663-676., 2006.
T. Gilbert, TL Sellaro, SF Badyak: "Decellularization of tissues and organs." Biomaterials, vol. 27, Issue 19., pp. 3675-3683., 2006.
HC Ott, B Clippinger, C Conrad, C Schuetz, I Pomerantseva, L Ikonomou, D Kotton, JP Vacanti. "Regeneration and orthotopic translplantation of a bioartificial lung." Nat. Med., vol. 16., Issue 8.,pp. 927-933., 2010.
JJ Song, SS Kim, Z Liu, JC Madsen, DJ Mathisen, JP Vacanti, HC Ott, "Enhanced in vivo function of bioartificial lungs in rats." Ann Thorac Surg, vol. 92., Issue 3., pp. 998-1005., 2011.

\* cited by examiner

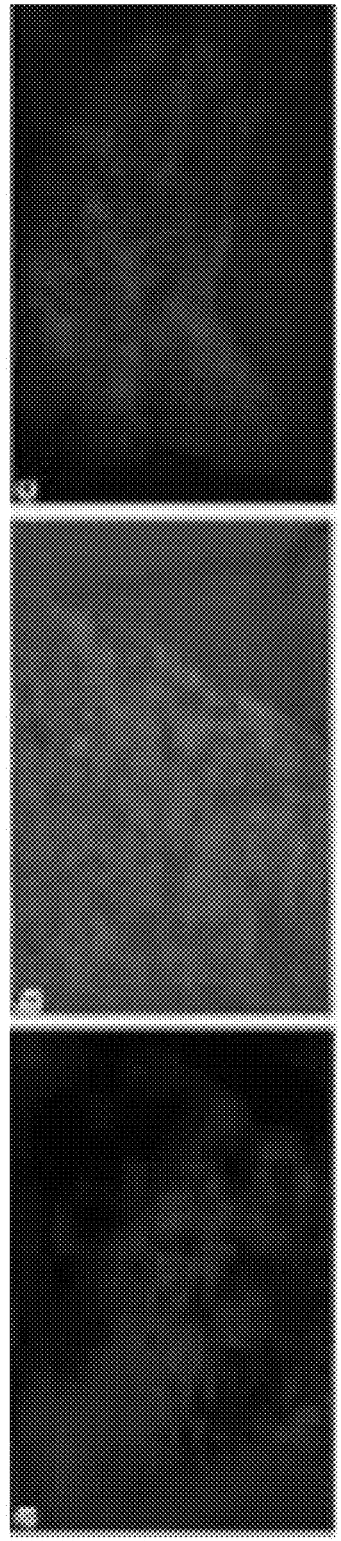

BJL with Ultrasonic Transducer

FUNCTIONAL RECOVERY OF HUMAN LUNGS FOR TRANSPLANTATION

CROSS-REFERENCE TO RELATED APPLICATIONS

This application claims the benefit of U.S. Provisional Application No. 61/808,621, filed Apr. 4, 2013 and claims the benefit of U.S. Provisional Application No. 61/920,117, filed Dec. 23, 2013.

FIELD OF THE DISCLOSED SUBJECT MATTER

The disclosed subject matter relates to a system for functional recovery of human lungs for transplantation. Particularly, the presently disclosed subject matter relates to a device for the recovery of human lungs and other organs that would otherwise be of insufficient quality for a successful transplantation.

BACKGROUND

Nearly 25 million people suffer from end-stage lung disease in the United States alone, with a staggering ~400,000 patients dying each year. Lung transplantation, the only definitive treatment for these patients, remains hampered by a severe shortage of donor organs, to the extent that only one out of four patients waiting for a lung undergoes transplantation. A variety of methods and systems are known for performing transplantation of lungs. However, lungs with insufficient gas exchange capacity are not suitable for transplant, resulting in a substantial reduction in the potential donor pool and a shortage of suitable donor lungs.

Conventional methods do not exist for recovering the functionality of lungs in order to render otherwise non-viable lungs suitable for successful transplantation. There thus remains a need for a method and system for recovering the functionality of lungs rejected for transplantation based on insufficient gas exchange capability or other conditions rendering non-viable lungs for transplantation.

BRIEF SUMMARY

Generally, the disclosed subject matter relates to the functional recovery of a low quality donor lung for transplantation. In some instances, the donor lung has been rejected for transplantation into a recipient. The disclosed subject matter includes a method of transforming a rejected donor lung into a lung viable for transplantation into a recipient. A decellularizing fluid is perfused through the donor lung. Simultaneously, a lung preservation fluid is perfused through a portion of a vasculature of the donor lung. The decellularizing fluid removes cells from the donor lung to define a decellularized region. The decellularized region is repopulated with cells from the recipient.

In some embodiments, the decellularizing fluid is perfused through at least one air pathway of the donor lung. The air pathway may include at least one bronchus. In some embodiments, the decellularizing fluid is CHAPS solution. In some embodiments, the decellularized region of the donor lung is along an air pathway of the donor lung. In some embodiments, the decellularized region is repopulated with pulmonary progenitor cells. In some embodiments, the lung preservation fluid is PERFADEX® solution. In some embodiments, the lung preservation fluid is perfused through the portal vein. In some embodiments, the decellularized region of the donor lung is preserved in at least one of composition, architecture, or mechanical properties. In other embodiments, tissue surrounding the decellularized region of the donor cell is preserved in at least one of composition, architecture, or mechanical properties. The tissue preserved surrounding the decellularized region may be parenchyma tissue. In some embodiments, the decellularized region of the donor lung is limited, thereby preserving properties of the decellularized region of the donor lung. The properties of tissue surrounding the decellularized region may also be preserved. In some embodiments, the decellularizing fluid is perfused through the parenchyma of the donor lung.

In another aspect, a medical device is provided to achieve the methods of the present disclosure. The medical apparatus includes a first cannula adapted for insertion in the bronchus of a lung. The medical apparatus also includes a second cannula adapted for insertion in the pulmonary artery of the lung. A first fluid reservoir is in fluid communication with a first pump and with the first cannula. A first fluid of the first fluid reservoir circulates through the first cannula by the first pump. A second fluid reservoir is in fluid communication with a second pump and with the second cannula. A second fluid of the second fluid reservoir circulates through the second cannula by the second pump. In some embodiments the first fluid is CHAPS solution. In other embodiments, the first fluid is culture medium. In some embodiments the second fluid is PERFADEX® solution.

In another aspect, a device for treatment or removal of cells from a lung Is provided. The device includes an outer tubular member having a longitudinal axis disposed between a proximal end and a distal end. The device also includes an inner tubular member coaxially disposed within the outer tubular member having a longitudinal axis between a proximal end and a distal end. The distal end of the outer tubular member includes a plurality of openings to permit fluid communication between the outer and inner tubular members.

In some embodiments, the proximal end of the outer tubular member includes a luer. In some embodiments, the distal end of the outer member includes a tip region. In some embodiments, the tip region is tapered. In some embodiments, the inner tubular member has a distal end including a reverse taper. In some embodiments, the plurality of openings includes oblong shaped openings having a length less than about ¼ inch. In some embodiments, the outer tubular member is adapted to remove decellularization reagents introduced by the inner tubular member. In some embodiments, the inner tubular member is adapted to introduce decellularization reagents to a lung. In some embodiments, the device further includes an ultrasound transducer.

In another aspect, a system for perfusion is provided. The system includes an outer tubular member having a longitudinal axis disposed between a proximal end and a distal end. The system also includes an inner tubular member coaxially disposed within the outer tubular member having a longitudinal axis between a proximal end and a distal end. The distal end of the outer tubular member includes a plurality of openings to permit fluid communication between the outer and inner tubular members. The inner tubular member is operatively connected to one or more containers comprising lavage or decell solution.

In some embodiments, the system also includes a pump to pump the lavage or decell solution into the device. In some embodiments, the lavage or decell solution is pumped into the inner tubular member of the device. In some embodiments, at least one of the inner or outer tubular members includes an ultrasound transducer.

In another aspect, a system for perfusion is provided. A first cannula is adapted for insertion in the bronchus of a lung. The first cannula has a distal end and a proximal end. A second cannula is adapted for insertion in the pulmonary artery of the lung. The second cannula is disposed within the first cannula. A first fluid reservoir is operably connected to a first pump and to the first cannula such that a first fluid of the first fluid reservoir is withdrawn from the first cannula by the first pump. A second fluid reservoir is operably coupled to a second pump and to the second cannula such that a second fluid of the second fluid reservoir is circulated through the second cannula by the second pump.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIGS. 6A-6H depict staining of cells between d44 and d55 of the 'distal' protocol according to an embodiment of the present disclosure for CC-10, Mucin2, SP-B, NKX2.1, AcTub, Mucin1 and lysozyme.

FIG. 6I depicts staining of cells cultured from d16 to d26 on ECM for NKX2.1 and p63 according to an embodiment of the present disclosure.

DETAILED DESCRIPTION

Figure 1:
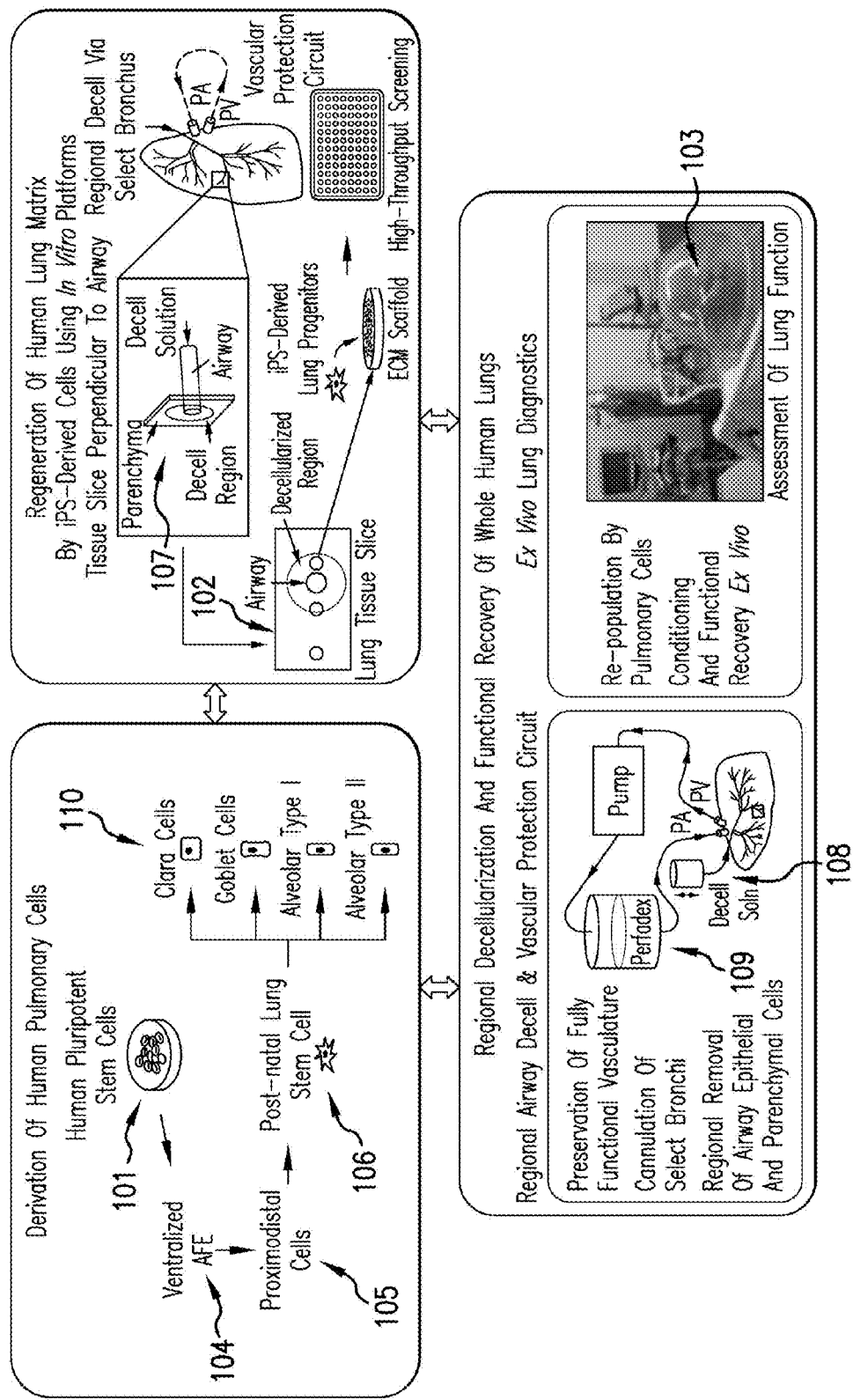
FIG. 1 is a schematic representation of a method and system in accordance with an embodiment of the present disclosure.

Reference will now be made in detail to exemplary embodiments of the disclosed subject matter, an example of which is illustrated in the accompanying drawings. Methods and corresponding steps of the disclosed subject matter will be described in conjunction with the detailed description of the system.

The methods and systems presented herein pertain to recovery of transplant lungs that are not viable using prior techniques. The disclosed subject matter is particularly suited for increasing the gas exchange of a donor lung so as to make it suitable for use.

The methods and systems of the present disclosure permit bioengineering of chimeric human lung by using rejected donor lungs and the recipient's pulmonary cells. This approach can be used to recondition acutely injured lungs while the patient is on ECMO support. In addition, the methods and systems of the present disclosure may be used to generate region-specific hydrogels from a variety of organs other than lungs. Such region-specific hydrogels can be combined with other biomaterials to create hybrid bioactive materials.

According to an embodiment of the present disclosure, a method to functionally recover low-quality human lungs rejected for transplantation is provided, by a combination of flow conditioning, regional decellularization, and infusion of cells. Donor lungs rejected for transplantation are taken, cells are removed from limited regions of the lung while preserving the composition, architecture, and mechanical properties of the decellularized matrix and the surrounding intact lung parenchyma. By simultaneously perfusing decellularization fluids through the lung parenchyma and PERFADEX® solution (or other suitable preservation fluid) through the portal vein, intact lung vasculature is preserved. The decellularized regions are then repopulated by the recipient's cells to produce a lung that is capable of an acceptable level of gas exchange.

The enormous complexity of the human lung, with its highly hierarchical vascular and bronchial architectures that create a large (~70 m$^2$) surface area for gas exchange, poses a challenge to recovery of functionality. In an aspect of the present disclosure, donor lungs not suitable for transplantation are used. The lung parenchyma is regionally decellularized while preserving the composition, architecture, and mechanical properties of the extracellular matrix. By simultaneously perfusing decellularization fluid through the lung parenchyma and oxygenated PERFADEX® solution through the vascular compartment, this method preserves intact lung vasculature. Decellularized regions are then repopulated with the patient's iPSC-derived pulmonary cells to bioengineer a functional chimeric human lung that will be capable of gas exchange and of gradual, beneficial remodeling.

The methods of the present disclosure permit the bioengineering of chimeric human lungs by using rejected donor lungs and the recipient's iPSC-derived pulmonary cells. This approach can be extended to reconditioning acutely injured lungs while the patient is on ECMO support. The repopulation of regionally decellularized lung tissue by pulmonary cells improves the quantitative understanding of the factors and mechanisms of lung regeneration, through synergistic and topologically specific regulation of the regenerative cells in a chimeric setting.

In one aspect of the present disclosure, functional populations of human pulmonary cells are derived from human pluripotent stem cells (hPSCs). Staged cell induction and differentiation enables identification of a population of renewing postnatal stem cells for lung regeneration.

In another aspect of the present disclosure, iPSC derivatives are cultured on slices of decellularized tissue from various regions of the human lung, to determine their ability to respond to the native matrix and to interact with the adult lung cells from the neighboring regions of the lung. This aspect provides for lung regeneration via a biomimetic system designed to mimic the early lung development.

In another aspect of the present disclosure, rejected donor lungs are functionally recovered to the level necessary for transplantation. In some embodiments, functional recovery comprises regional decellularization and repopulation of the lung parenchyma and the preservation of intact and functional vasculature of the lung.

As with many other organs, the supply of donor lungs is limited, and long-term outcomes of transplantation remain hampered by chronic rejection and opportunistic infections. To address these challenges, tissue engineering approaches may be adopted that use scaffolds, cells, and bioreactors to bioengineer lung substitutes. Due to the extremely complex hierarchical structure of the lung, a highly specialized matrix is required to support the engraftment and function of diverse populations of cells. Decellularized rat lungs can be repopulated by primary epithelial and endothelial lung cells and participate in gas exchange upon transplantation. However, such lungs are subject to failure after only a few hours, largely due to the clotting of blood entering the lung parenchyma through leaky vasculature damaged by decellularization. In addition, these techniques may not scale up to the human lung that contains ~700 million alveolar sacs with billions of pulmonary cells.

Embryonic and induced hPSCs can be stimulated to form ventralized anterior foregut endoderm (AFE) from which the lung is developmentally derived. AFE derived from human embryonic and iPS cells can be differentiated into proximal and distal pulmonary cells and give rise to cells with characteristics of postnatal stem cells. HPSCs can be introduced into pulmonary lineages at various stages of differentiation to study their regenerative capacity.

Instead of studying cell specification and differentiation in monolayers or embryoid bodies, the cells are infused into thin three-dimensional slices of decellularized human lung tissue matrix, which is the native milieu for growth and differentiation of these cells. The native matrix of the lung will provide cells with topologically specific signals and attachment sites. By harvesting lung tissue from various anatomical locations, the topological regulation of cell function is shown; by regional decellularization and repopulation of lung tissue, a chimeric lung setting is formed for studying cell interactions.

In an aspect of the present disclosure, whole human lungs undergo functional recovery by replacing nonfunctional cellular material with fresh therapeutic cells. First, the whole lungs are decellularized, and only segments in the lung are repopulated, which permits the use of lower cell numbers and facilitate active remodeling in the chimeric lung containing the residual cells and exposed matrix. Second, lungs are decellularized by perfusion through airways in a manner that preserves the full functionality of the vascular network, such that the donor lung remains perfusable by blood and nonthrombogenic.

Referring to FIG. 1, a chimeric human lung suitable for transplantation is bioengineered by repopulating rejected donor lungs with iPS-derived pulmonary cells. A partially decellularized lung matrix guides the differentiation of seeded iPS-derived pulmonary cells by synergistic effects of the tissue matrix (composition, architecture, biomechanics) and parent cells (mature pulmonary phenotypes). This effect can be tested by: (i) Deriving pulmonary progenitors from embryonic stem cells (ESCs) and induced pluripotent cells (iPSCs), collectively termed human pluripotent stem cells (hPSCs) 101 and culturing them on decellularized lung matrix to study topological regulation of their fate and function, (ii) bioengineering lung tissue by culturing these cells in partially decellularized lung slices 102, and (iii) studying functional recovery of the whole lung 103 ex vivo.

Cell lines may include hESCs: RUES2; iPSCs: HDF2, HDF9. Derivation of human pulmonary cells includes formation of ventralized AFE 104 and its early differentiation into proximal pulmonary lineages (PP) 105, distal pulmonary lineages (DP) 105, and putative fetal or postnatal stem cells 106. Lungs unsuitable for transplantation are procured, decellularized, and either processed into slices 107 for cell culture or subjected to whole-lung perfusion. Lungs are decellularized by perfusion through the bronchial tree 108, while the lung vasculature will be protected by concomitant perfusion with PERFADEX® solution 109. A 96-well plate platform is established in which hPSC-derived pulmonary progenitors are studied on scaffolds cored from lung slices 102 (fully decellularized, transient and intact regions) for their ability to mature and regenerate lung tissue. The whole lungs are decellularized, seeded with cells, cultured for 17 days with medium perfused through the airway, and PERFADEX® solution 109 through the vascular compartment, and switched to ventilation-perfusion to evaluate gas exchange.

Interpretation of data related to derivation of human pulmonary cells is based on the molecular cues and times necessary for induction, specification, and differentiation of each cell phenotype. The yields and stability of pulmonary cell populations and their function on the lung matrix may thereby be optimized. Interpretation of data related to regeneration of human lung matrix by IPS-deriver cells using in vitro platforms is focused on cell-cell interactions in the chimeric lung setting, and the progression of remodeling. For analysis of regional decellurization and functional recovery of whole human lungs, functional recovery of the lung may be defined as a function of regional decellularization/repopulation and the time of conditioning. Data collected from each of these three processes may be used to heuristically establish additional design criteria and measurable indicators for bioengineering of the chimeric lung.

The individual and interactive effects of variables may be determined by multi-way analysis of variance (ANOVA) using, for example, SAS 8.0 for Unix. For post hoc comparisons of means between different experimental groups, Tukey's test may be used in conjunction with one-way ANOVA.

HPSCs 101 are differentiated into functional lung lineages 110—Clara, mucous cells, ciliated cells, neuroendocrine cells, basal cells, alveolar type I and type II cells (ATI and ATII), as well as renewing stem cell populations. Ventral AFE 104 are induced from hPSCs 101 and differentiation into pulmonary lineages 110.

The respiratory tract and lungs are derived from two buds on the anterior ventral aspect of the definitive endoderm. The lung buds grow and branch in a stereotyped pattern, with the proximal and distal aspects giving rise to the conducting airways and alveolar progenitors, respectively. Subsequently, the airway epithelium specializes, with the emergence of basal, goblet, Clara, ciliated, and other cell types. The alveolar progenitors slowly mature to give rise to ATI and ATII cells. Adult lung contains several cell populations capable of regenerating lung and airway epithelium after injury. HPSCs may be induced into cells similar to such postnatal lung stem cells, or into fetal stem cells capable of renewal, expansion, and differentiation. Generating and expanding such cells from patient-specific iPSCs allows repopulation of decellularized regions of the lung, as these cells are naturally endowed with the capacity to regenerate damaged lung parenchyma and airways.

Several putative lung stem cells appear to function after damage have been identified. Mouse studies have identified a bronchoalveolar stem cell (BASC) expressing both SP-C (an ATII marker) and CCSP (a Clara cell marker). Lineage tracing has showed that alveoli are not regenerated from CCSP$^+$ or SP-C$^+$ cells. Instead, a lung stem cell with a CD49f$^+$ (integrin β6) CD104$^+$Epcam$^{hi}$CD24$^{lo}$ phenotype gave rise to airway and alveolar cells in vitro. Rare α4β6 (CD49f$^+$) cells were also located in the terminal bronchioles and alveoli. Generation of both Clara and basal cells may be critical to lung regeneration, as Clara cells can generate ciliated cells and function as transit amplifying cells in bronchioles, whereas basal cells make up 30% of the epithelium of the large airways, have regenerative capacity in mice, express Ngfr and CD49f, and form so-called tracheospheres in vitro. As human pseudostratified epithelium reaches to the bronchioli, the phenotype, function and location of stem cells may differ from those in mice. Bronchiolar p63$^+$ cells migrate through the pulmonary mesenchyme to repair alveoli, as NKX2.1$^+$FOXA2$^+$ structures surrounded by p63$^+$ cells are generated from hPSCs in vitro.

Lung progenitors are derived from the AFE 104 by sequential application of regulatory factors, and their function are evaluated by cultivation on decellularized lung matrix 102. This derivation is performed using hESCs (RUES2). In this manner, large numbers of specialized cells are generated suitable for use in regeneration of human lung matrix and functional recovery of whole human lungs. A protocol is also established for the human iPSCs (lines HDF2 and HDF9).

Differentiation of hPSCs into Ventral Anterior Foregut Endoderm (AFE)

After inducing definitive endoderm by Activin A, AFE fate (FOXA2+SOX2+EPCAM+) is induced by combined inhibition of BMP (NOGGIN) and TGF-β (SB431542) signaling. Transplantation under the kidney capsule of immunodeficient mice shows that these cells give rise to AFE derivatives, including tubular structures that express the lung marker SP-C. Subsequent application of developmental ventralization signals (Wnt3a, BMP4, FGF10, KGF and EGF) induces markers of ventral anterior foregut, including pharyngeal endoderm (PAX1, PAX9, TBX1) and lung (NKX2.1, GATA6, p63, FOXJ1, FOXP2). Inclusion of retinoic acid (RA) favors the lung fate over pharyngeal fate consistent with the developmental of RA in lung bud specification.

Preferential Specification of Lung Field Over Pharyngeal Endoderm

Figure 2:
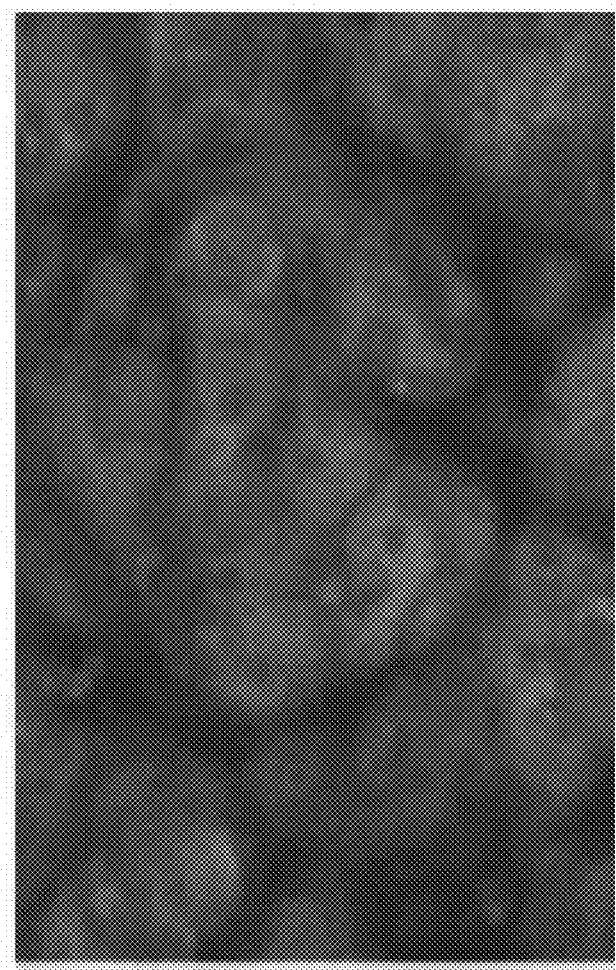
FIG. 2 depicts staining for NKX2.1 (green) and FOXA2 (bluish green) in optimized conditions according to an embodiment of the present disclosure.

FIG. 2 shows staining for NKX2.1 (green) and FOXA2 (bluish green) in optimized conditions. AFE-fated cells pass through a zone where the Nodal/Activin inhibitor (Lefty) and BMP4 inhibitor (Noggin) are expressed. This explains why blocking TGF-13 and BMP signaling after exposure to Activin A is required to specify this part of the endoderm. Subsequently, the most anteriorly fated cells are exposed to the Wnt inhibitor, Dkk1. Inhibiting Wnt signaling results in a finer specification of the lung field. Sequential application of NS (d6) followed by SB+IWP2 (Wnt inhibitor SI) (d7) increased the fraction of NKX2.1$^+$FOXA2$^+$ cells and the NKX2.1 mRNA at d15 after ventralization. Reversing the NS/SI sequence or using SI alone was detrimental to NKX2.1. These manipulations, at 50 µM RA, resulted in the majority of the cells expressing NKX2.1+FOXA2+.

Induction of Proximal Fate

Figure 3:
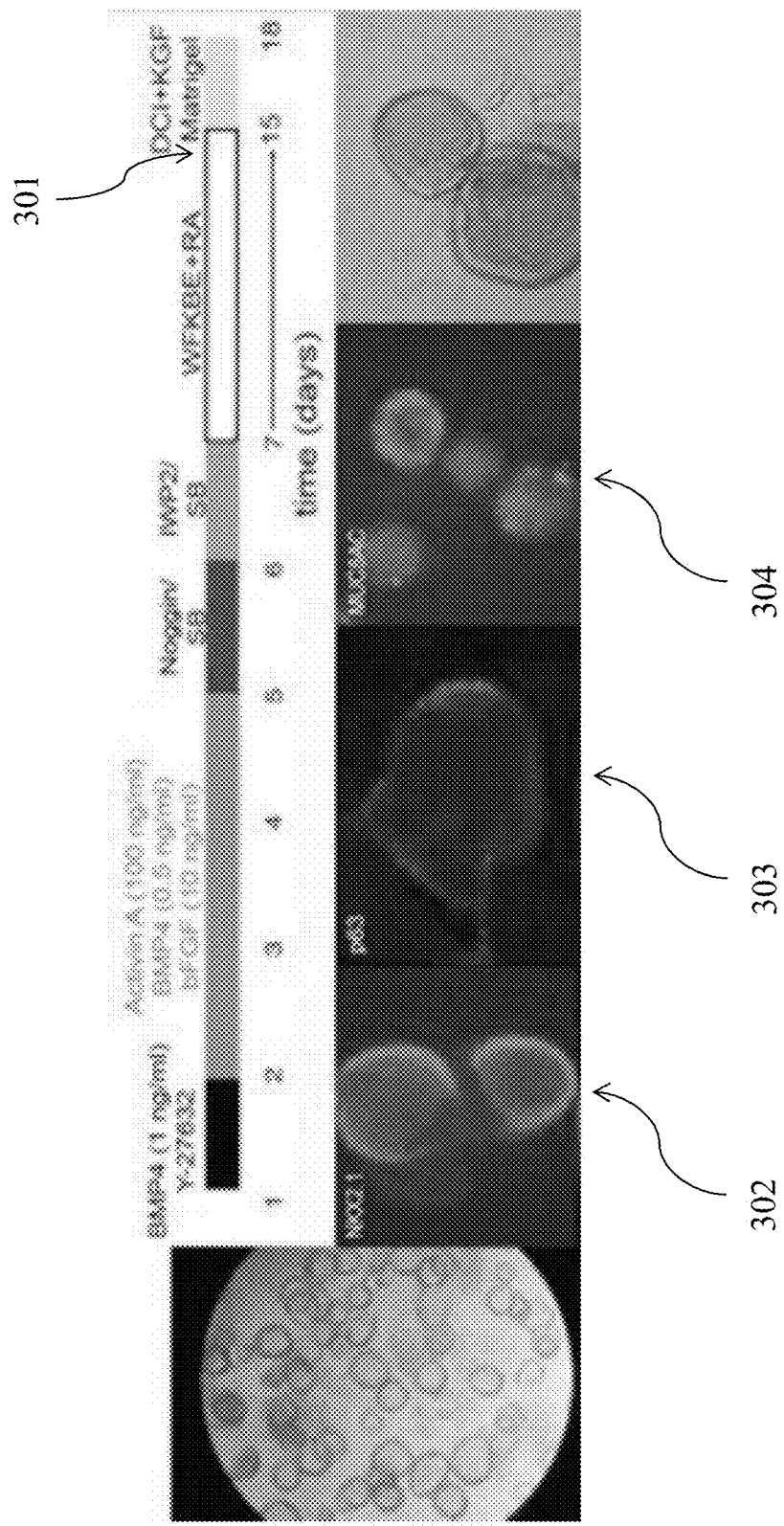
FIG. 3 depicts colony morphology and expression of NKX2.1, p63 and MUC5AC after plating AFE ventralized in the presence of WFKBE+RA in DCI and Matrigel according to an embodiment of the present disclosure.
Figure 4:
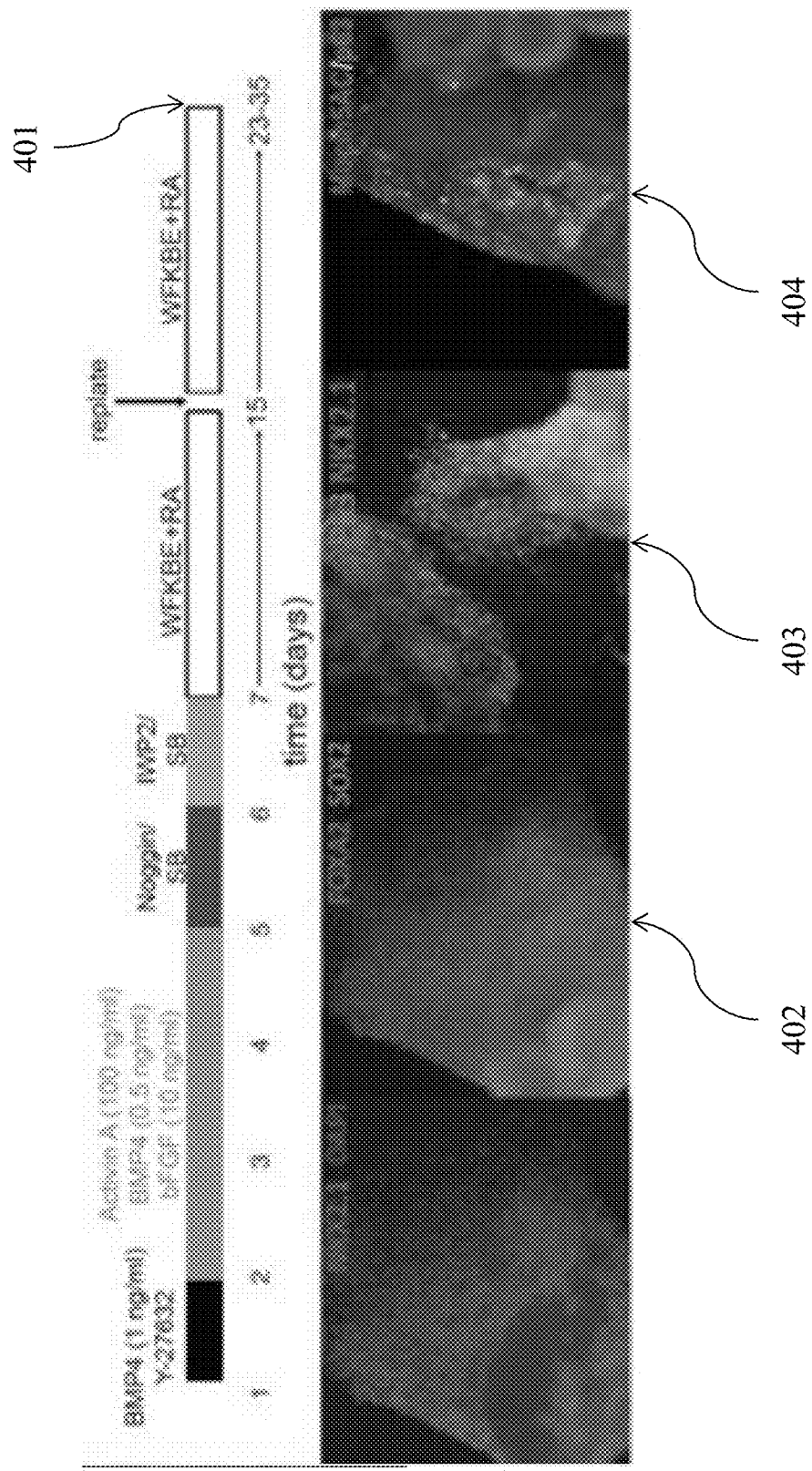
FIG. 4 depicts cells cultured under 'proximal' conditions for 35 days stained for NKX2.1, p63, FOXA2, SOX2 and MUCIN5AC according to an embodiment of the present disclosure.

Turning to FIGS. 3 and 4, at day 15 301, the cells are replated under two distinct conditions: (1) Matrigel culture in maturation medium (DCI: dexamethasone, butyrylcAMP and isobutylmethylxanthine) that induces alveolar maturation in fetal mouse lung explants. This forms large spherical structures that are reminiscent of adult tracheospheres and expressed NKX2.1 302, p63 303, and MUC5AC 304 (goblet cell marker). (2) Replating in ventralization conditions (WFKBE+RA): upon continued treatment to d23-35 401, the cell colonies are >90% FOXA2+SOX2+ 402, with the majority expressing NKX2.1 403. The colonies are surrounded by a rim of p63$^+$ cells, suggestive of basal cells, the stem cells of the large airways. Towards the center of the structures, p63 and NKX2.1 are co-expressed, suggestive of differentiation of p63$^+$ cells into NKX2.1$^+$ cells. Within the colonies, tubular structures are present that express the mucins MUC2 and MUC5AC (404).

Induction of a Distal Fate

Figure 5:
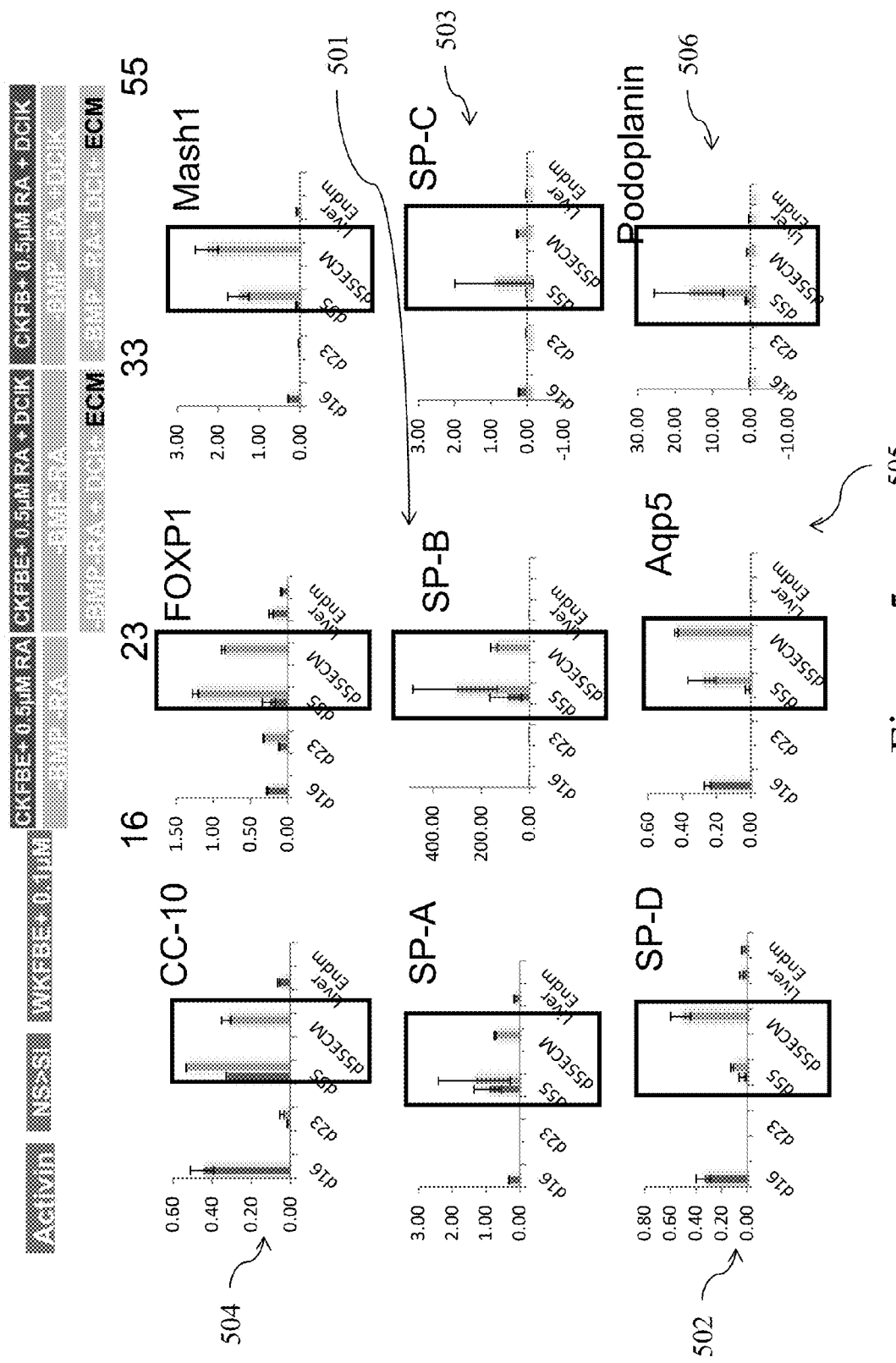
FIG. 5 depicts qPCR analysis of cells cultured according to an embodiment of the present disclosure at days 16, 23, 33 and 55.

Turning to FIG. 5, constitutively active RA signaling prevents distal lung development, and favors proximal airway development. BMP4 needs to be removed to achieve expression of the distal marker, SP-C. These data indicate that both BMP4 and RA are detrimental for distal lung development in vitro. An extended culture period is thus appropriate in either WFKBE+RA or WFK (i.e., without BMP-4 and RA) and added the DCI (maturation) medium at day 33 of culture. As a third culture condition, cells are cultured on slices of decellularized human lung matrix. By qPCR, expression of distal markers (SPB 501, SP-D 502, and to lesser extent SP-C 503), as well as the Clara cell marker CC-10 504, the neuroendocrine marker MASH1, and the ATI markers Aqp5 505 and Podoplanin 506 are achieved at day 55, both with and without ECM. These cultures contained virtually every type of lung epithelial cells: Clara cells (CC-10 504), goblet cells (MUC1, mUC2, MUC5AC), ciliated cells (acetylated tubulin), and ATII cells (SP-B 501). The ATI markers, AQP5 505 and podoplanin 506, are observed at the mRNA but not at the protein level.

The above discussion shows that lung and airway lineages can be generated from hPSCs at high purity, and with the capability of manipulated proximodistal differentiation.

Expression of lung markers are followed at different stages of development (days 15, 25, 35, and 55). FOXA2, NKX2.1, and GATA6, that mark all lung domains, are used to define lung-committed cells. As proximodistal differentiation proceeds, each of the Clara cell marker CCSP, the ciliated cell marker FOXE, the mucus cell markers (MUC2, MUC5a), the neuroendocrine marker (calcitonin gene-related peptide product (CGRP) and MASH1, and the markers of terminal alveolar differentiation SFTPC (SP-C), SFTPA (SP-A) and SFTPB (SP-B) (ATII), and Aq5 and T1a (ATI) are quantitated.

Factors Involved in Proximodistal Differentiation

Continuing culture in WFKBE+RA leads to a more proximal fate, while switching to conditions without BMP4 and RA induces a more distal fate. These conditions may be refined by proceeding in the following stepwise fashion:
1. Determine whether all factors in the cultures are required and whether their concentration can be optimized, as many morphogens show concentration-dependent effects.
2. Remove Wnt in the proximal condition to enhance a proximal fate, as Wnt signaling is developmentally important to establish a distal fate.
3. Test the effects of non-canonical Wnt (Wnt5a), as it plays a role in distal lung development, likely through regulation of SHH and FGF10 signaling.
4. Block Notch signaling using the gamma-secretase inhibitor DAPT, to mimic early developmental signaling that promotes a more distal fate.
5. Once the conditions that specify proximal fate are refined, determine whether Notch and SHH affect differentiation in proximal regions.

Because Notch signaling at the final stage determines fate choices among the three mature cell types of the bronchial tree by favoring Clara cell fate and regulates differentiation of basal cells, the inhibition of Notch signaling by DAPT is of interest. Because SHH affects differentiation of neuroendocrine cells through direct effects, not mediated by the mesenchyme, blocking/enhancing SHH signaling may affect differentiation in vitro.

Cell Expansion

Differentiation of hPSCs in vitro proceeds remarkably fast relative to the rate of human development in vivo. The effect of G-CSF (which enhances differentiation of cardiomyocytes) is examined under conditions for induction of the lung field considered to be optimal. An essential hormonal system for growth during development is the IGF—growth hormone (GH) axis. Thus, addition of IGF1, GH, or both, increases cellular yield. This approach is supported by the observation that in mutants with defective IGF signaling, lungs are severely hypoplastic.

Effect of Timing

The timing of addition or removal of factors affects the outcome, as the potential to express ventral AFE markers in the presence of WFKBE is only present during a narrow window time after NS induction. Thus, timing may be varied to determine the optimal conditions for proximal and distal differentiation.

Postnatal Lung Stem Cells

Colonies of spheroids expressing NKX2.1, FOXA2, and p63 are obtained using DCI medium for 3 days. Application of 'tracheosphere' conditions does not induce the formation of such spheres, and the markers for more mature cells are not present. These data indicate that these cells originate from a relatively early progenitor cell and have not been cultured long enough to achieve full maturation, which may be tested by extending the time in culture. These colonies of spheroids instead represent renewing lung-committed stem cells. This may be tested by dissociating the colonies and replating them either in the same conditions (DCI) or under conditions for the generation of tracheospheres. The colonies may be analyzed for expression of p63, MUC5a, FOXJ1, acetylated tubulin (ciliated cells), CCSP (Clara cells), and CRPP (neuroendocrine cells), SP-C (ATII cells), T1", AQ5 (ATI cells). The expression of more mature markers may become evident or that the potential to differentiate will only be acquired when the progenitor has developed further. This will expose the differentiating cells to the (proximal) WFKBE+RA or (distal) WFK conditions for a longer time before plating in DCI or tracheosphere conditions.

Figures 6D, 6E, 6F:
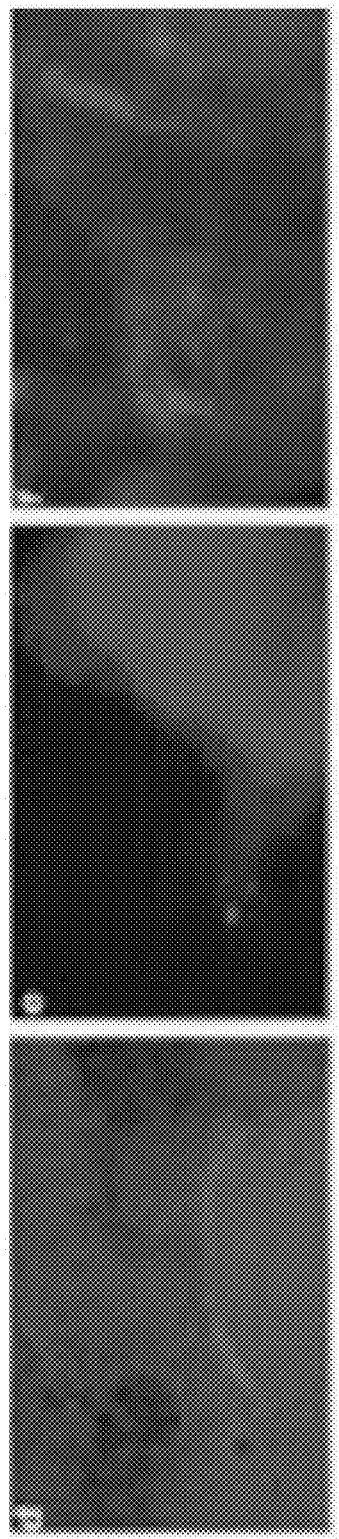
Figures 6G, 6H, 6I:

Turning to FIG. 6, after exposure of the AFE to WFKBE+ RA and replating at days 15-19, colonies containing MUC5a+ tubular structures surrounded by p63$^+$ cells are obtained. A fraction of these cells develops into spheres after plating in Matrigel and DCI media. The peripheral p63$^+$ NKX2.1lo cells are more primitive cells in these colonies. These putative stem cells can be prospectively isolated by analyzing the cell populations for surface markers associated with stem cells in the lung (NGFR, CD49f, EPCAM, CD24, ALDH (using a colorimetric stain ALDEFLUOR), both prior to formation of the spheres and in the spheres themselves. The p63$^+$ cells at the periphery of the colonies and those lining the spheres will express stem cell markers (α6β4 integrin CD49f). Expression of other reported markers for mammary gland stem cells are monitored (since the mammary gland also shows branching morphogenesis), and in particular c-KIT, CD10, CD133 and CD90. Cell populations expressing any of these markers are isolated by cell sorting, and plated in conditions that generate spheres. Limit dilution analysis reveals the frequency of sphere initiating cells, and determines whether the formation of the spheres is dominated by one cell type.

Conditions for the growth of postnatal putative lung stem cells are applied to hPSCs to generate cells consistent with postnatal lung stem cells. This is done by replating, after sorting for cells expressing putative stem cell markers (see above), in conditions reported for tracheospheres and for lung stem cells.

The cell populations derived are systematically tested for their efficiency at repopulating decellularized human lung matrix according to the methods of this disclosure. Desired cell types can be specified using such a biomimetic niche. The cells in the DCI-induced spheres, may be substituted.

To obtain mature, defined populations a screening approach can be alternatively applied. In such an approach, cells are plated in 400 binary combinations of a select number of factors in 48-well plates, and are subsequently pooled in groups of 4-6 for qPCR analysis for a desired marker. Where the desired marker is expressed, the conditions in pools of positive wells are set up, and then qPCR is performed on cells cultured in individual conditions. This approach leads to conditions for the induction of SP-C. Instead of soluble factors, an approach involving inhibiting specific transcription factors using RNAi may be used. Colonies or spheres can thereby be expanded. Alternatively, conditions established for postnatal stem cells on NIH 3T3 feeder cells may be used.

Regeneration of Partially Decellularized Human Lung Matrix by hPSC-Derived Cells One approach to bioengineering whole organs is to decellularize the organ and repopulate it with appropriate cells expecting that: (a) the cells will recognize their native location within the matrix, (b) the cells will attach and differentiate in a location-specific manner, and (c) the new organ will gradually regain function. This approach requires removal of donor cells and their replacement with autologous cells. However, this approach exhibits several disadvantages, including: (a) High numbers of cells needed to repopulate the whole lung, (b) the lack of important cell-derived signals, and (c) the lack of innate lung function. These limitations can be overcome by creating "pockets" of decellularized tissue within the lung while maintaining the viability of remaining lung tissue and preserving the lung vasculature. This approach allows for a reduced number of cells needed to repair the lung and support some level of lung function after transplantation. A lung recipient would still require immunosuppression, possibly at a decreased level as the lung parenchyma remodels and the autologous cells take over. The interactions between the repair cells, the exposed matrix, and the residual donor cells determine the viability of this approach. The cells residing in intact regions of the lung provide site-specific signaling to the hPSCs to differentiate into appropriate cell types at appropriate locations. The effects of decellularization on pulmonary differentiation of seeded cells is determined by systematically testing different regions of the lung, decellularized to different extents, and seeded with different populations of cells derived according to the methods discussed above.

Because the extracellular matrix (ECM) provides structural and mechanical support to the cells as well as a source of biological signals (growth factors, chemokines, cytokines), it plays an important role in cellular attachment, growth, and differentiation. Each organ contains an intrinsic, unique ultrastructure, providing an "ideal" scaffold with the characteristics necessary to promote growth, differentiation, and maintenance of resident cells. A lung may be decellularized and reperfused to repopulate their ECM. With the size and complexity of human lung, it is desirable to avoid decellularization and repopulation of the entire lung. The level of decellularization and the parent cells, individually and interactively, affects the attachment, growth, and differentiation of lung progenitor cells. The parent (donor) cells and matrix provide site-specific signals for lung progenitor cells to differentiate into specific pulmonary lineages.

According to one aspect of the present disclosure, decellularized lung matrix and the mature cells from adjacent regions of intact lung tissue synergistically regulate the hPSC-derived pulmonary cells in a topologically specific manner, leading to functional recovery and remodeling of the donor lung tissue. To this end, human lungs rejected for transplantation are washed, the vascular network is protected by PERFADEX® perfusion or other suitable preservation solution, and the airway perfused with decellularization solutions. Different levels of decellularization are achieved by varying the dwell of the solution within the airway. Following regional decellularization, the lungs are processed and areas of interest are dissected and sliced. There are three different regions of interest (non-decellularized, partial-decellularized and fully decellularized) and each region is seeded with hPSC-derived lung progenitors of various types (derived according to the methods discussed above) to study cellular differentiation and assembly.

Decellularization of Human Lungs

In all tissues, ECM provides structural and mechanical support for the resident cells and a source of growth factors, chemokines, and cytokines ECM structure and composition play major roles in cellular attachment, growth, and differentiation, making the tissue-specific ECM an ideal scaffold material for cell differentiation and functional assembly. Fully decellularized tissues such as heart and bone provide highly cell-instructive templates, both for the in vitro formation of engineered tissues and the in vivo delivery of therapeutic cells. Lungs can be decellularized in a number of ways both known in the art and set out herein. According to one embodiment of the present disclosure, perfusion is performed with salt solutions and detergents with decellularization times ranging from a few hours to over a month. Retention of the ultrastructure of the lung matrix is an accepted benchmark for success of decellularization. Decellularization methods according to various embodiments of the present disclosure include: (1) 3.8 mM SDS, (2) 16 mM 3-[(3-Cholamidopropyl) dimethylammonio]-1-propanesulfonate (CHAPS), and (3) a 4-Step method using 0.02% trypsin, 3% Tween-20, 4% sodium deoxycholate, and 0.1% peracetic acid, to determine which method effectively removes cellular material while best maintaining the composition, architecture and biomechanical properties of the ECM. These properties are best preserved after CHAPS decellularization.

To perform regional decellularization, human lungs that have been rejected for transplantation are procured, the connective tissue removed, and the cell viability maintained by immersion of lungs in cold PERFADEX® solution during transport to the perfusion system. The pulmonary artery is cannulated and the vasculature perfused with PER- FADEX® solution by a peristaltic pump to protect the vascular tree. One of the main bronchi is cannulated and perfused using hydrostatic pressure with CHAPS solution. Different dwell times are used to achieve different levels of decellularization. Pen/Strep is added to all solutions to eliminate native and pathological bacteria from the lung. Regions with airway branches may be dissected and slices cut perpendicular to the airway and maintained viable in culture using established methods.

In some embodiments, alternative preservation solutions may be used. In general, solutions similar to PERFADEX® solution, containing about 5% dextran 40 (Mw 40,000), $Na^+$ 138 mmol, $K^+$ 611 mmol, $Mg^{2+}$ 0.8 mmol, $Cl^-$ 142 mmol, $SO_4^{2-}$ 0.8 mmol, $H_2PO_4^-$ plus $HPO_4^{2-}$ 0.8 mmol and glucose 5 mmol per 1,000 ml.

Following decellularization, the airway is perfused with 0.8% agar (40° C.) solution using hydrostatic pressure. The lung is then allowed to cool at 4° C. to solidify the agar. Biopsy cores (7 mm in diameter) are taken from the intact region, the transition region and from the decellularized region. Each core is secured by fibrin glue to the bottom of the well in a 96-well plate for cell culture experiments with hPSC, or used for evaluation of DNA content (biochemically), viability of residual cells (live-dead assay), matrix architecture (histology) and the amounts and distributions of matrix proteins (including collagens, laminin, fibronectin, elastin, by immunostain). Tissue slices are cultured in M-199 medium supplemented with bovine insulin (1.0 "g/ml), hydrocortisone hemiacetate (0.1 "g/ml), retinyl acetate (0.1 "g/ml), and 100 U/ml pen/strep, the conditions shown to support cell viability in lung slices for up to 60 days.

hPSC derivatives are cultivated on slices of decellularized human lung tissue. In the lung, cells are modulated by coordinated actions of soluble signals, the composition, architecture and mechanical properties of the matrix, and the physical stimuli associated with blood flow and ventilation. For such a hierarchically organized tissue, spatially homogeneous scaffolds fall short of providing an adequate regulatory milieu. Instead, native ECM is an appropriate template for regeneration.

Figure 7A:
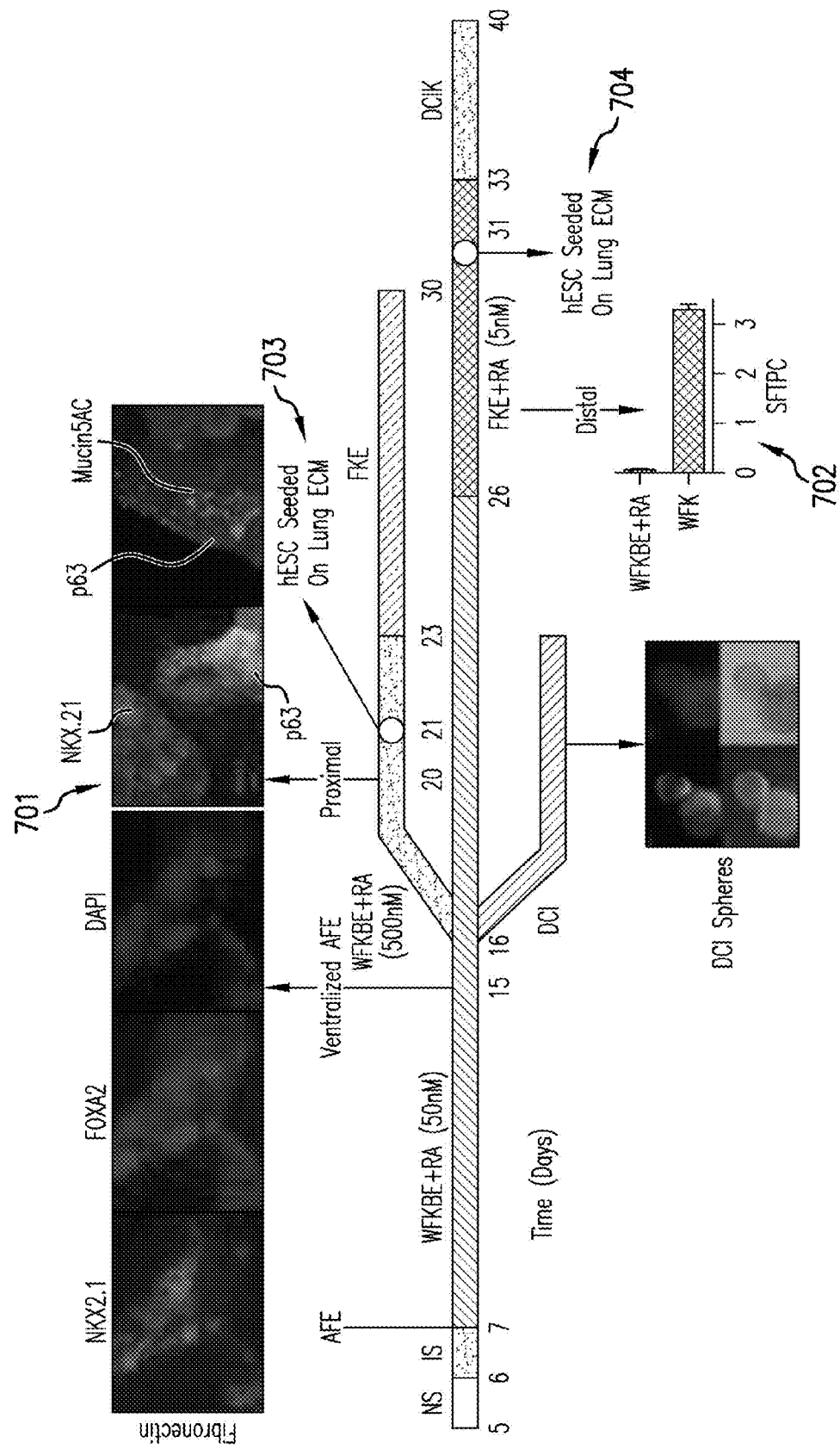
FIG. 7A depicts the differentiation of hESCs on decellularized human lung matrix by a differentiation protocol in according to an embodiment of the present disclosure.
Figure 7B:
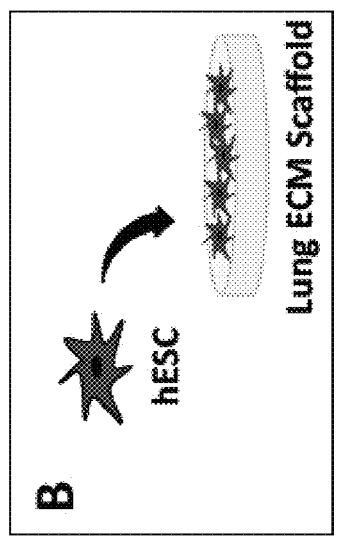
FIG. 7B depicts seeding of hESCs on lung ECM scaffolds according to an embodiment of the present disclosure.
Figure 7C:
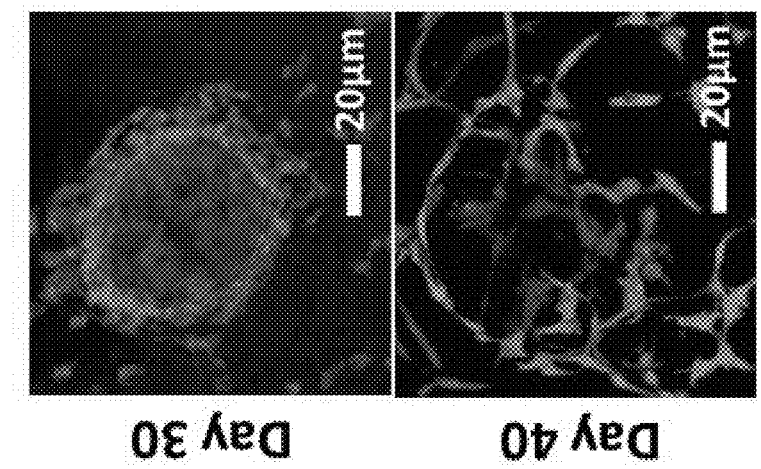
FIG. 7C depicts Calcein AM live staining of proximal ventralized AFE showing compact lumen structure (day 30, top) and distal ventralized AFE showing formation of ring-like structure (day 40, bottom) according to an embodiment of the present disclosure.
Figure 7D:
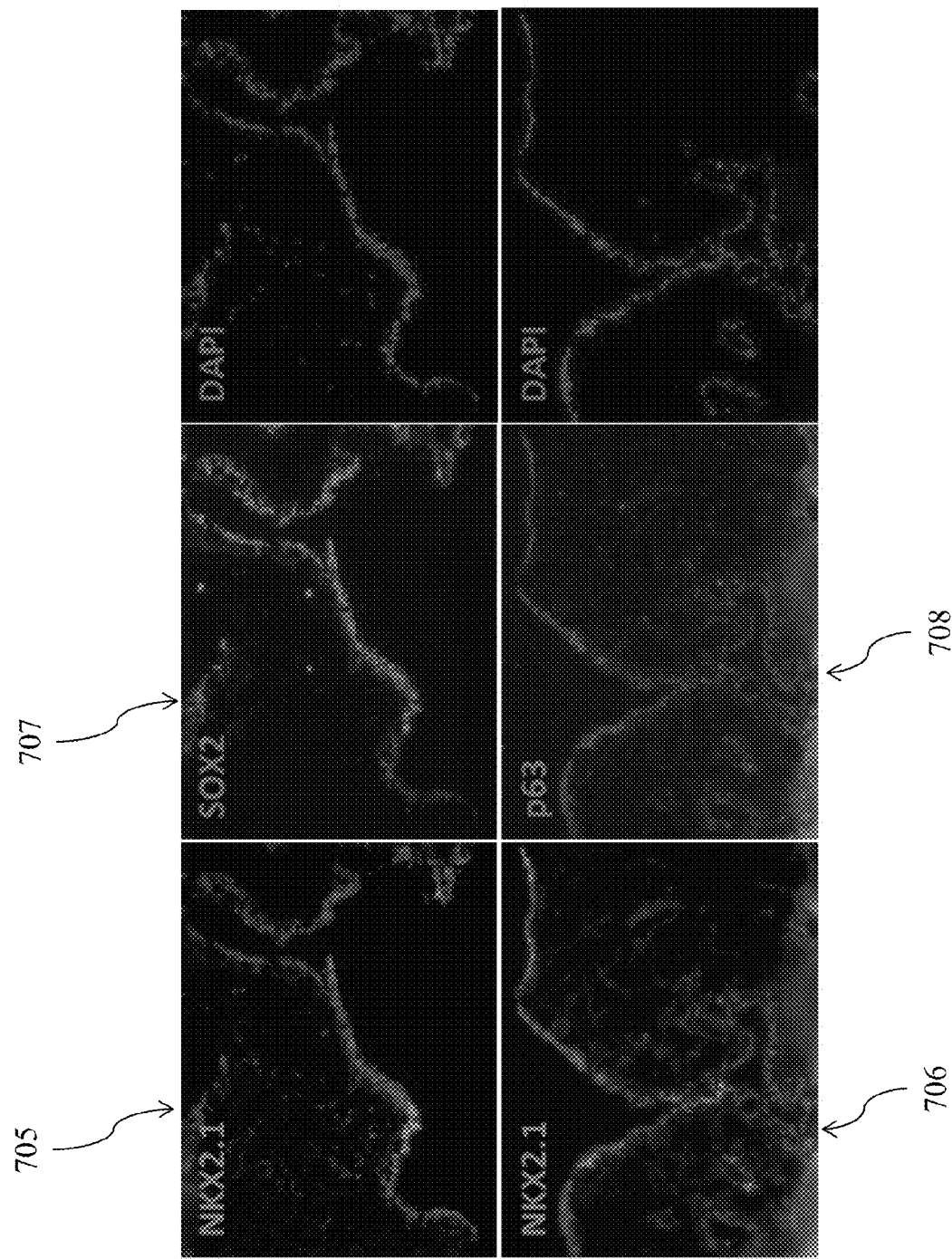
FIG. 7D depicts proximal ventralized AFE showing co-localization of NKX2.1 and SOX2 (day 30, top) and NKX2.1 and p63 (day 40, bottom) according to an embodiment of the present disclosure.

Turning to FIG. 7A, Following the protocols described above, pulmonary progenitors from embryonic hPSCs are directed into proximal 701 and distal 702 airway epithelial fate, and seeded into lung matrix at day 21 703 and 31 704, respectively. After 9 days of culture on lung matrix, live confocal imaging of cells specified to a proximal ventralized AFE (FIG. 7B) and distal fate (FIG. 7C) show >90% viability and interesting formation of ring-like structures after cell culture on lung matrix in the distal conditions. After 11 days of culture on lung matrix, cells express NKX2.1 (lung 705, airway 706) SOX2 (proximal airway 707) and p63 (proximal basal cells 708) (FIG. 7D).

Figure 8A:
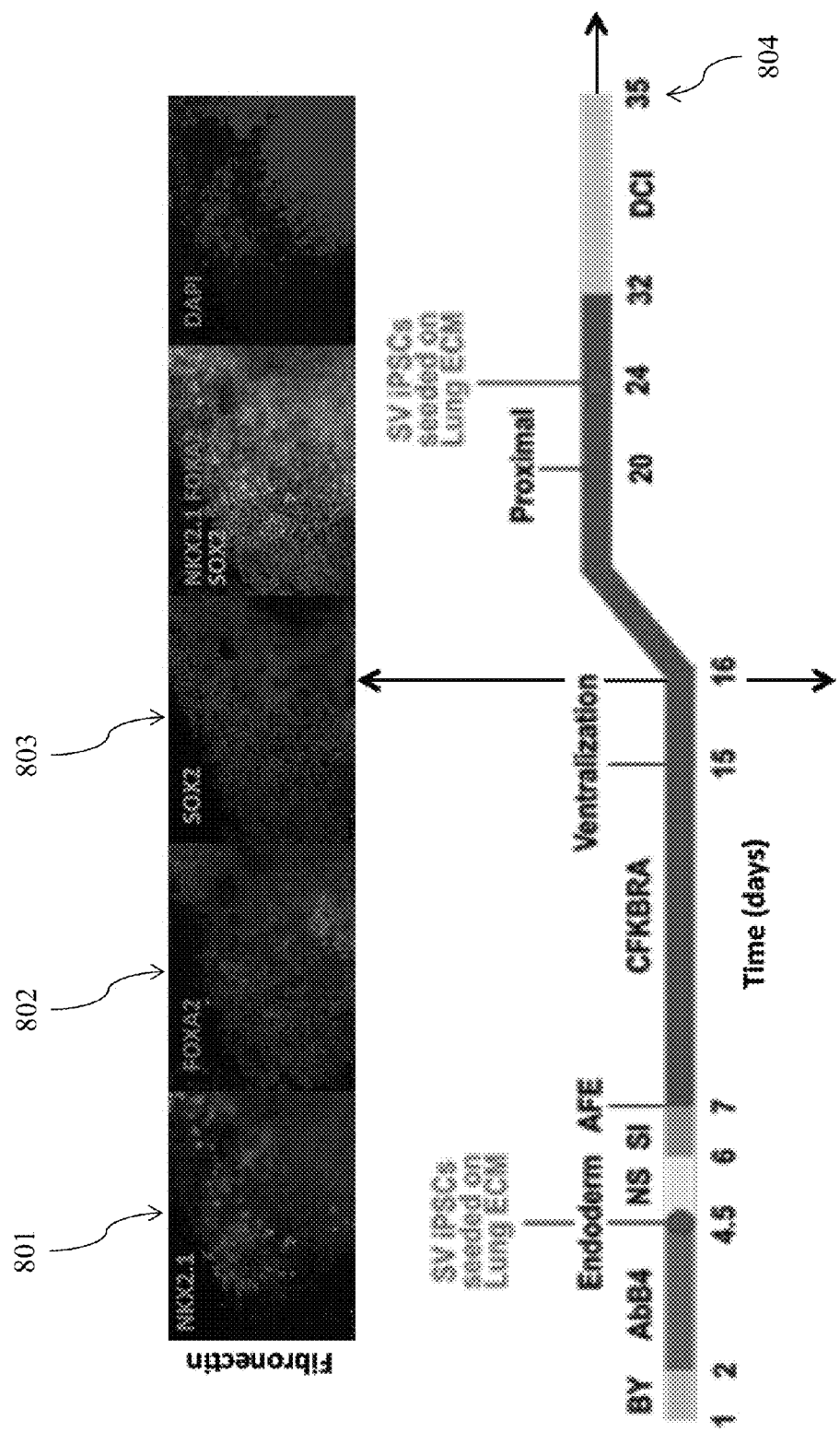
FIG. 8A depicts a differentiation protocol of iPSCs on decellularized human lung matrix according to an embodiment of the present disclosure.
Figure 8B:
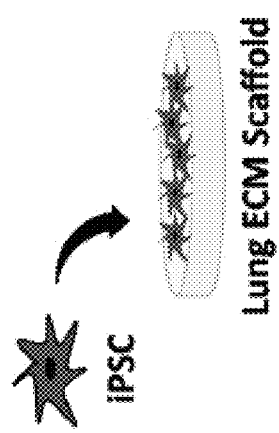
FIG. 8B depicts seeding of iPSCs on lung ECM scaffolds according to an embodiment of the present disclosure.
Figure 8C:
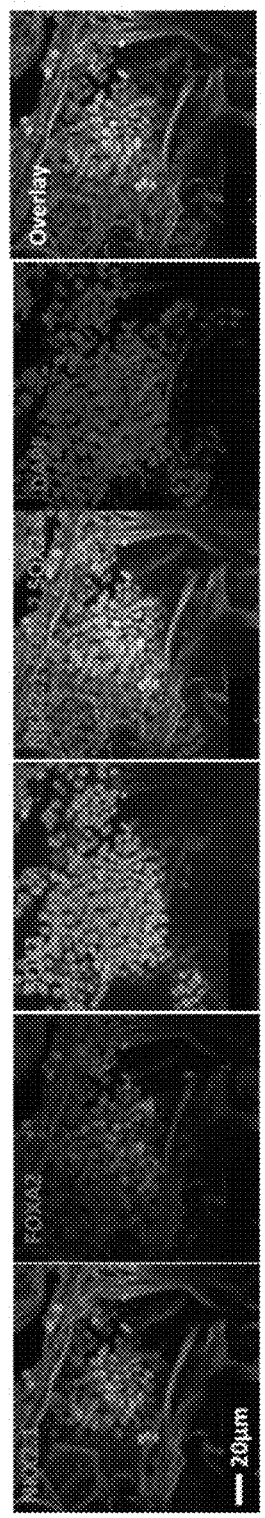
FIG. 8C depicts ventralized AFE differentiated on lung ECM from day 4.5 endoderm showing co-localization of NKX2.1, FOXA2, and SOX2 (day 16, top row) according to an embodiment of the present disclosure.
Figure 8D:
FIG. 8D depicts Clara cell precursors co-expressing SCGB3A2, NKX2.1, and FOXA1 (day 35, bottom row) according to an embodiment of the present disclosure.

Turning to FIG. 8, differentiation of iPSCs on decellularized human lung matrix also results in the formation of ventral AFE with co-localization of NKX2.1 801, FOXA2 802, and SOX2 803 expression (day 16, FIG. 8C). By day 35 804 and FIG. 8D, Clara cell precursors are identified that coexpress SCGB3A2, NKX2.1, and FOXA1.

Human lungs are procured according to an active IRB protocol and prepared as described above in the form of 7 mm discs that will be attached by fibrin to the wells in 96-well plates, and incubated in growth medium for 30 minutes. Prior to seeding, human iPS derived lung progenitor cells are labeled using DiI. Fresh medium with the suspended cells (a range of 50,000-200,000 cells per disc) are added to each well. These low cell numbers are feasible because of the significant cell growth on decellularized lung matrix.

The above procedure is performed with four cell types: ventralized lung-specified AFE at d15, proximal and distal pulmonary lineages at days 35-55, and stem cell spheres on the discs obtained from different regions of reg lung (as discussed above with regard to FIGS. 7 and 8). Over 7 days of culture, discs are monitored by microscopy (DiI label), and processed for assessing cell growth (DNA by PicoGreen), viability, metabolism (Alamar blue), proteins (immunostains, arrays), and gene expression (qPCR).

This procedure illustrates the topological regulation of hPSC pulmonary cells by the tissue matrix (derived from different proximal and distal regions of the lung) and the donor cells in the transient and intact tissue regions. The alveolar microarchitecture and function (barrier, biomechanics, expression and secretion of surfactant proteins) is reestablished. Taken together, these outcomes define sets of conditions for repopulation of the whole lungs.

If the DiI label is lost during culture, cell transfection may be used. Precise adjustment of the hydrostatic pressure (dwell) is necessary to establish lavage-type flow in and out of the lung without damaging delicate lung matrix. In addition, optimal flow conditions vary with the state of the lung. To overcome ambiguities in determining the flow conditions, mathematical modeling is used. Reduced viability and/or function of parenchymal cells may be addressed by using thinner slices (to minimize diffusional constraints) or with supplementation with ATP (to stimulate cell metabolism).

Regional Decellulerization and Functional Recovery of Whole Human Lungs

The lung is an organ with enormously complex hierarchical structure with numerous cell types that cannot be engineered by combining cells and simple scaffolds. Donor lungs for transplantation, which are already in short supply, are often rejected due to poor functionality (after being tested in extracorporeal perfusion apparatus). In one aspect of the present disclosure, their quality is improved by stem cell bioengineering. hPSC-derived pulmonary cells are used (to give rise to most if not all lineages of the lung) with decellularized lung matrix, which serves as a cell-instructive template through its largely preserved architecture, composition and mechanical function. Regionally decellularized lungs are used to reduce the numbers of cells required for regeneration and to augment topological regulation by the tissue matrix with signals generated by the neighboring resident cells. Regimens of decellularization, repopulation with cells and subsequent conditioning are provided to reconstitute lung function at levels acceptable for transplantation.

Two processes are coordinated to complete functional recovery: (i) removal of cells from limited regions of the lung while preserving the vascular bed, and (ii) repopulation of decellularized regions with pulmonary cells of different types. Both steps are conducted by perfusion through the lung parenchyma via selective airways. The regimen of perfusion, the extent of decellularization, and types and numbers of cells to be infused affect the progression of functional recovery. Functional recovery and lung remodeling are likewise correlated to the differentiation stage of the infused cells.

Adult human lungs do not regenerate beyond the microscopic level. Currently, the only way to replace lung tissue is by transplantation, a procedure that is hampered by the severe shortage of donor organs. Development of a bioartificial lung and any measures that would increase the number of usable lungs would help alleviate these problems. Alternative approaches to segmental or whole lung regeneration include regenerating trachea and large airways and pulmonary cells grown on polymer scaffolds to proliferate and form alveolar structures. In the system of the present disclosure, ECM defined the lung architecture and directs cell differentiation.

The creation of substantial lung tissue that can be ventilated through the patient's airway and perfused through the vasculature has previously been limited by the inability to generate a scaffold that can reproduce the branching alveolar and vascular architecture of the lung, support gas exchange, and retain the cartilaginous structure of the major airways. According to an aspect of the present disclosure, lungs rejected for transplantation are conditioned by autologous pulmonary progenitor cells delivered via the airways, while preserving the native vasculature in a bioreactor designed to mimic the environment of the developing lung just before the transition to air breathing. Such lungs are transplanted into a host and participate in gas exchange.

Turning to FIGS. 9 and 10, human lungs 901 rejected for transplantation are procured from a donor network in standard fashion, from donors who consented to lung donation for research. Lungs are transported to a medical center in PERFADEX® solution on ice. On arrival, the lobes are isolated. On each lobe, the bronchus 902 and the pulmonary artery 903 and vein 904 are cannulated to independently perfuse the airway and vasculature. The lungs are mounted onto an Ex Vivo Lung Perfusion (EVLP) system (FIG. 9B) in which the lung is perfused and ventilated under physiologic conditions. EVLP is a novel approach for evaluation and reconditioning of donor lungs that fail to meet criteria for transplantation in an effort to increase the donor pool. The pulmonary artery is perfused with oxidized PERFADEX® solution 905 for 7 days to protect the lung vasculature from any effects of decellularization and maintain its functionality. The bronchial tree is perfused with a series of solutions 906 in a protocol designed as a lung lavage, which is clinically used to remove excessive deposits of lipoproteins in patients with pulmonary alveolar proteinosis. Lung perfusion is done in four steps: (i) Wash and conditioning of the whole lungs, (ii) Regional decellularization (perfusion of, e.g., CHAPS through selected regions), (iii) Repopulation with cells (by infusion into decellularized regions), and (iv) Perfusion by culture medium for 7 days.

Figure 9A:
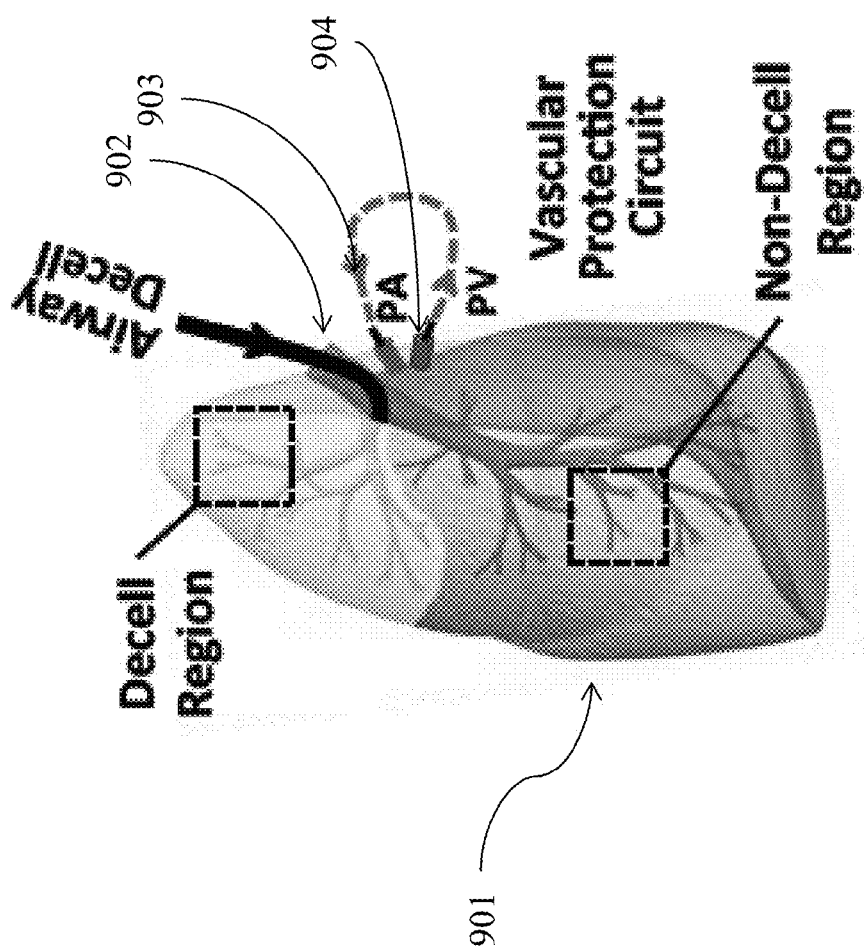
FIG. 9A is a schematic of the regional decellularization of the upper right lobe via select airway cannulation, with the vascular network protected via perfusion of the pulmonary artery (PA) and vein (PV) according to an embodiment of the present disclosure.
Figure 9B:
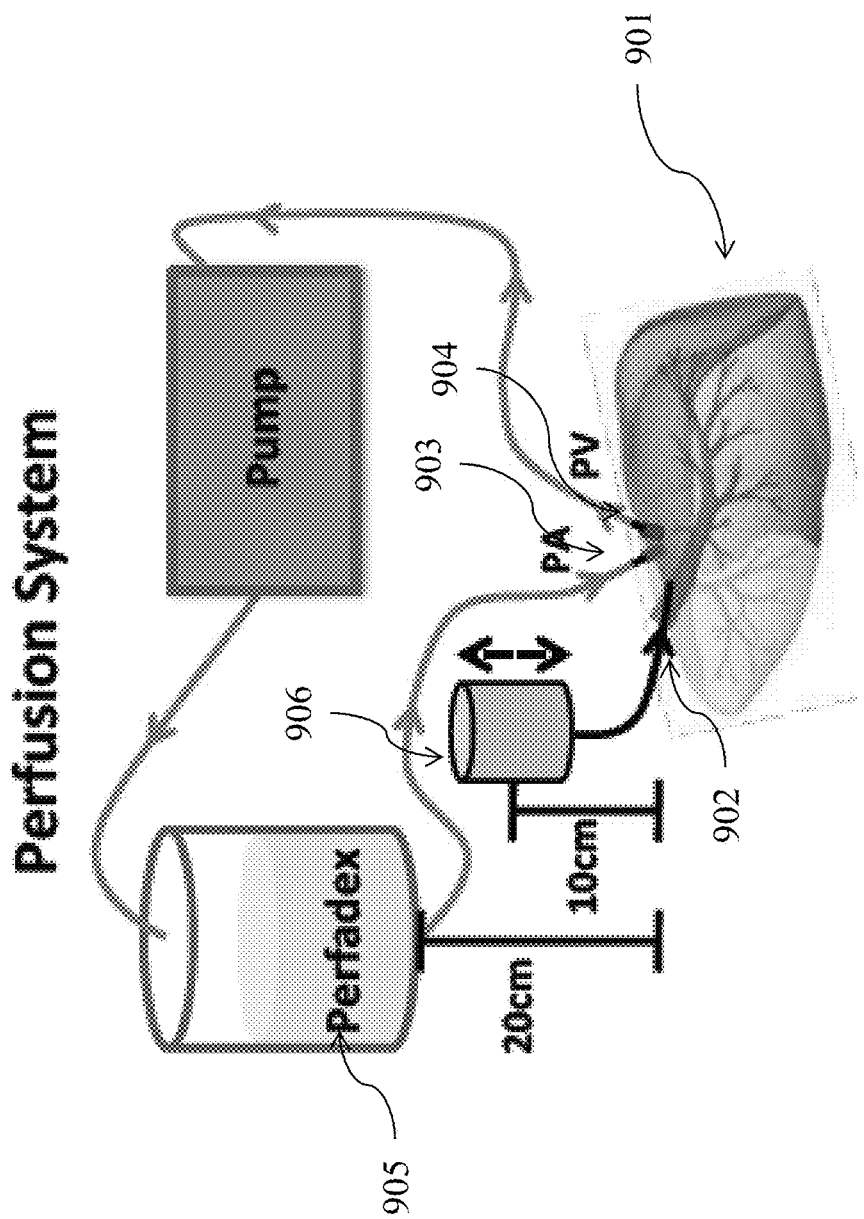
FIG. 9B is a schematic of a regional perfusion system according to an embodiment of the present disclosure.
Figure 9C:
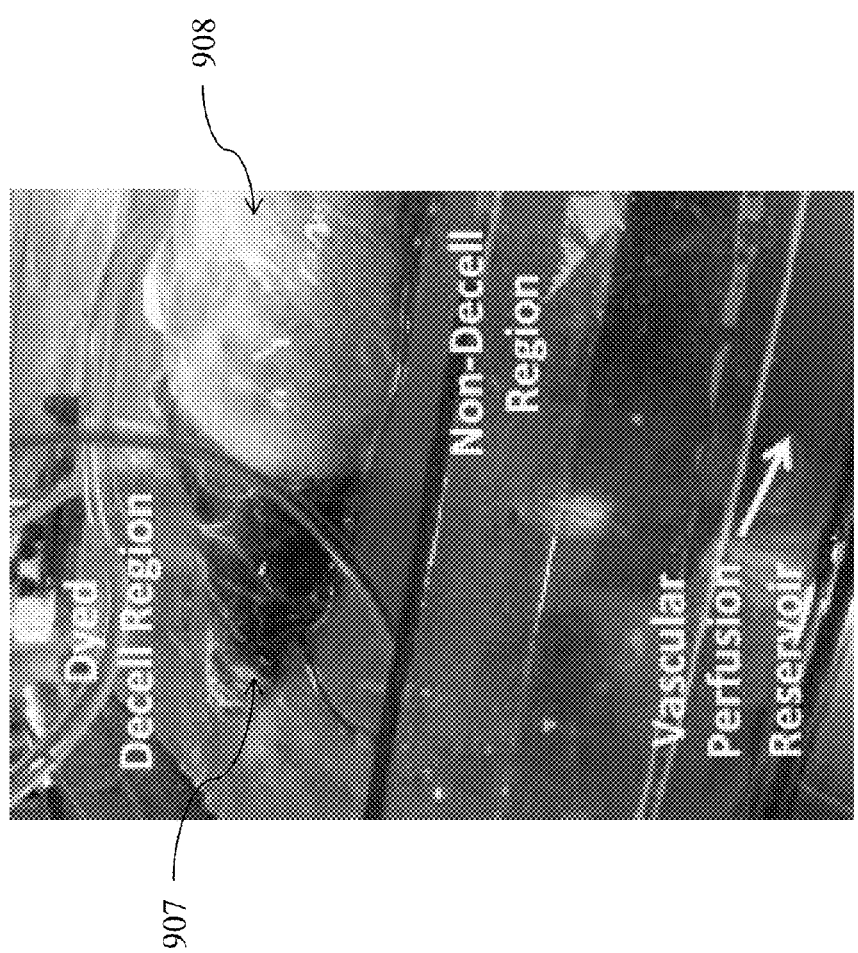
FIG. 9C is a photograph of an upper right lobe perfused with blue dye while pumping PBS through the vasculature according to an embodiment of the present disclosure showing no leakage of dye from the airway into the vasculature.
Figure 9D:
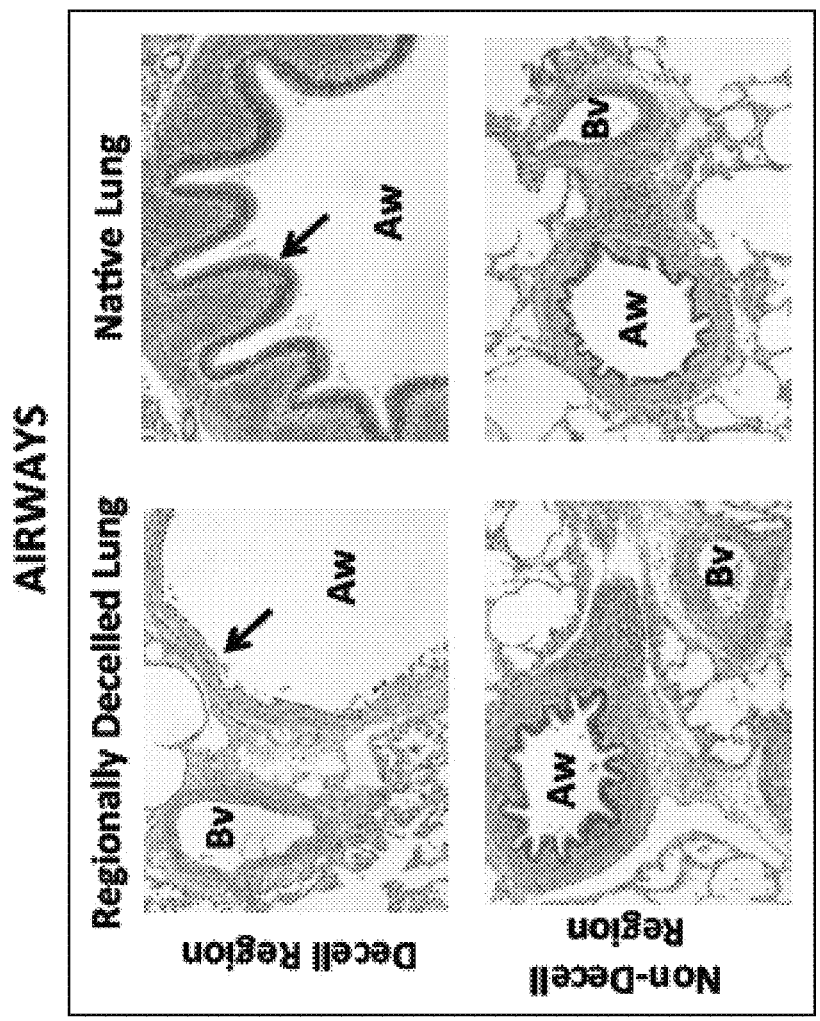
FIG. 9D depicts H&E of decellularized regions and native lung showing the removal of the epithelial layer in the airway according to an embodiment of the present disclosure.
Figure 9E:
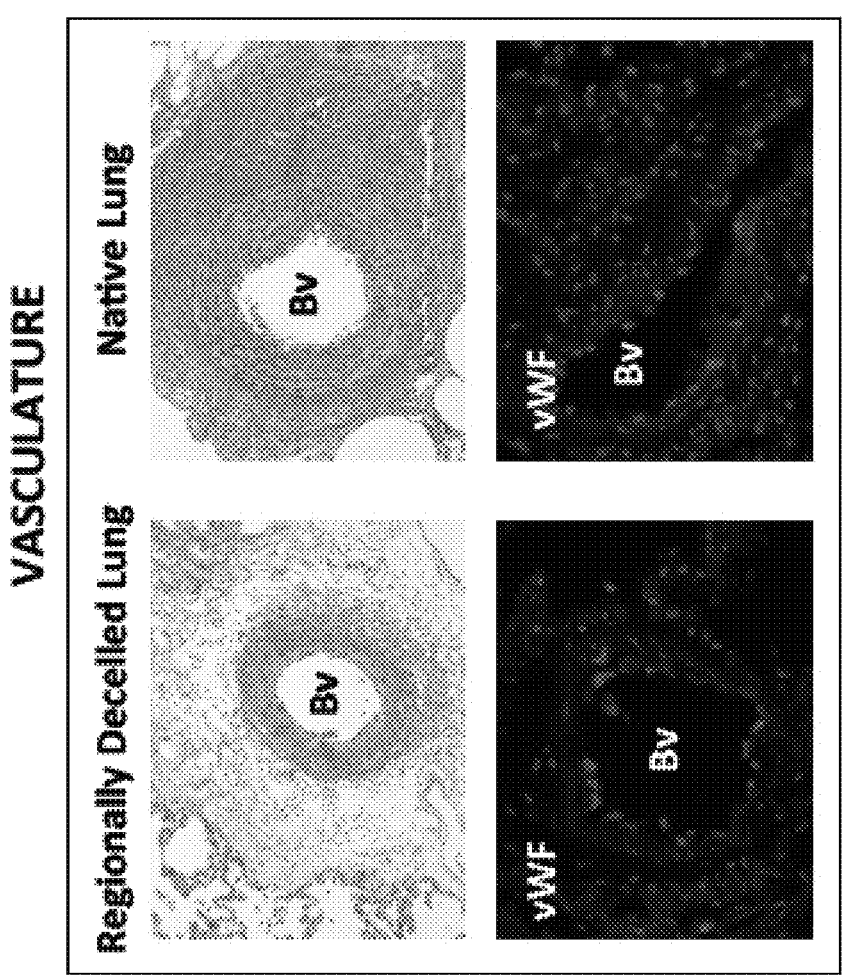
FIG. 9E depicts H&E and von Willebrand Factor (vWF) immunostaining of decellularized and native lungs indicating the vasculature is protected and remains intact during regionalized decellularization according to an embodiment of the present disclosure.
Figure 10A:
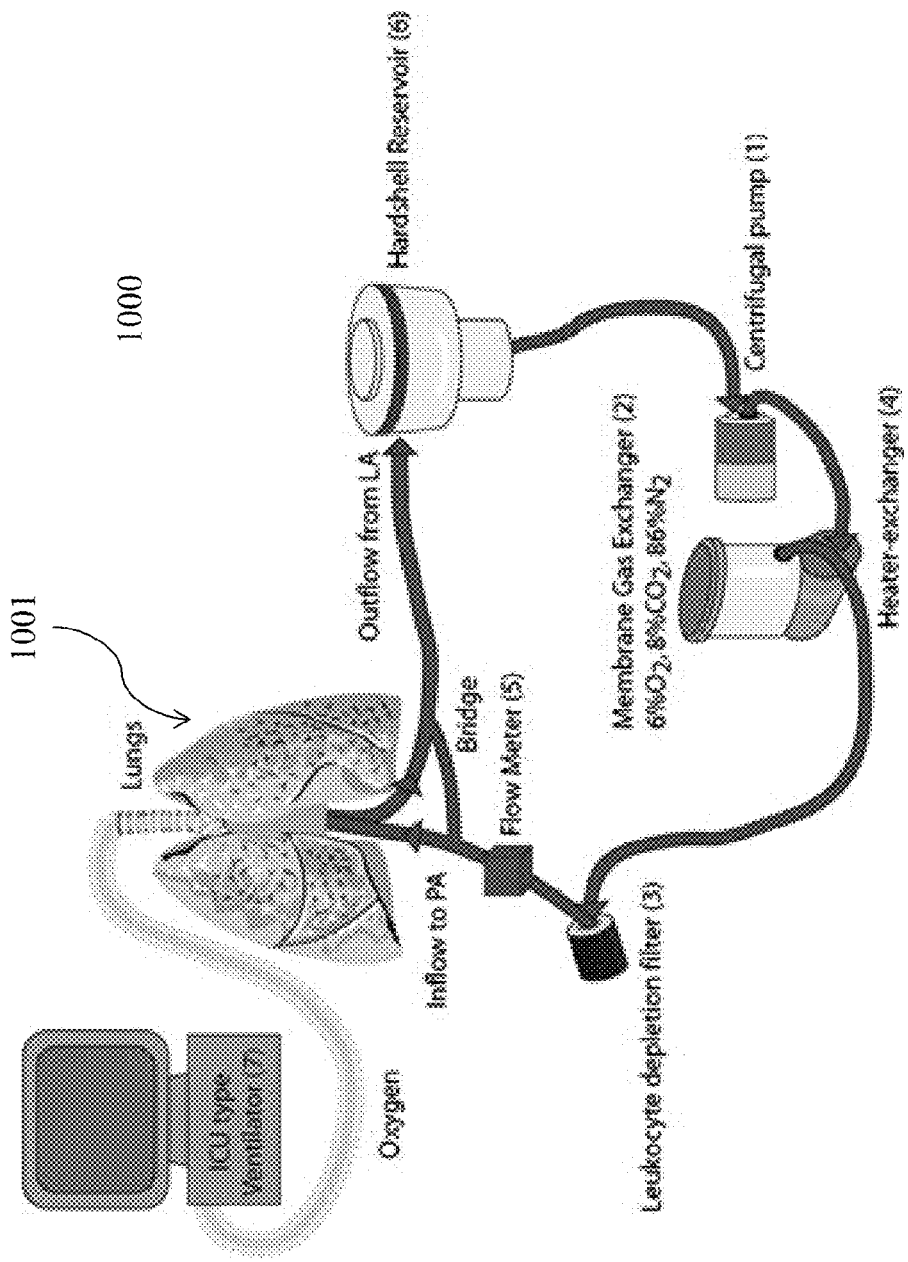
FIGS. 10A-10D depict a process of ex vivo perfusion and cultivation according to an embodiment of the present disclosure.
Figure 10B:
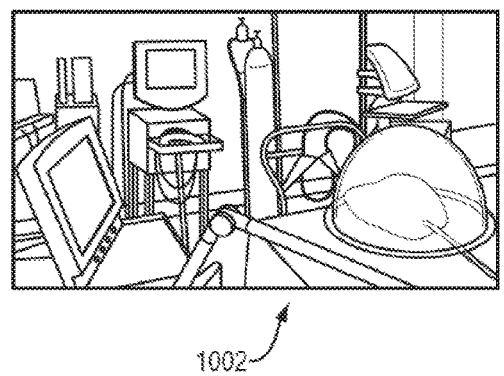
Figure 10C:
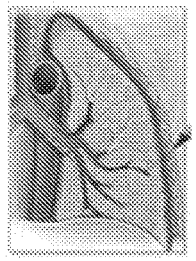
Figure 10D:
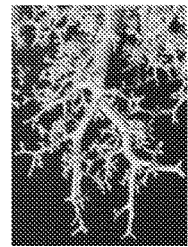

Function of the lung depends on the coexistence of a functional epithelium lining the surface of the airway-alveolar tree and a quiescent and confluent endothelium lining of the vascular tree. In both compartments, the cell phenotypes and organization are site-specific. Leaky vasculature will cause the failure of a bioengineered lung after only a few hours of implantation. To avoid the problem of leaky vasculature on the human scale, two approaches are provided: (i) decellularization of the lung by perfusion through the airway and preservation of intact vasculature, and (ii) regional decellularization, to reduce the number of stem cells to practically achievable levels and to maintain signaling of donor cells to guide the differentiation of hPSC-pulmonary cells. A whole lung or a lung lobe is cannulated and perfused through a distal airway branch by a series of isotonic and mild detergent solutions to achieve decellularization, and rinsed with PBS (FIGS. 9A and B). Decellularized regions 907 are surrounded by clearly demarcated intact tissue 908 (FIG. 9C). Slices are sectioned across these partially decellularized regions to show decellularized airway and an intact vasculature (FIGS. 9D and E). Layers of epithelial cells are removed while maintaining a viable vasculature as shown by the H&E and the positive stain for von Willebrand Factor (vWF) as shown in FIG. 9D.

Clearly delineated regions of decellularized tissue appear within regions of intact parenchymal tissue and intact vasculature (FIG. 9D). In some embodiments of the present disclosure two segments per lobe are decellularized, corresponding to ~10% of the lung volume. The segments are examined for retention of alveolar micro-architecture, cartilaginous lining of large airways, and functionality of the vascular bed. These protocols may be developed with the aid of mathematical modeling and matrix studies.

To repopulate decellularized lung regions, the cells are delivered through the airway, as during bronchoscopy, using 6 million cells per mL decellularized volume. Following cell seeding, the lung is dynamically perfused with culture medium through the trachea and with PERFADEX® solution through the pulmonary artery to induce regeneration of parenchyma and preserve vasculature. In some embodiments, cells that show the best regenerative capacity according to the protocols discussed above are used. The resulting cell distributions, viability, phenotypes, and functional recovery of the lung are observed.

On day 7, the lungs are transferred to the EVLP ex vivo system for functional assessment, by measuring lung compliance, pulmonary vascular resistance and functional gas exchange. Lung compliance is assessed under quasi-static conditions by ventilating the lung and measuring the pressure changes. The standard compliance parameters will be calculated from the measured pressure/volume dynamics of ventilation and pulmonary vascular resistance. Gas exchange is determined by deoxygenating the perfusate with nitrogen and measuring the oxygenation of the solution after perfusing through ventilated lung, with 50% of normal gas exchange used as a target value. These functional measurements have been used clinically for lung transplants, under conditions that are protective for both the lung airway and lung vasculature. Parallel samples of lung tissue are taken for detailed analyses of repopulated regions using methods discussed above.

Success criteria for seeding include the maintenance of alveolar microarchitecture and functional vasculature, the ability of the new tissue to provide barrier to particulates, and physiologic compliance. After blood perfusion is established, these lungs have an arterial pressure of #375 mm Hg for the inspired oxygen fraction of 1.0. Freshly explanted lungs are evaluated to determine baseline values of lung function. Decellularized lungs are evaluated to ascertain their function. Repopulated lungs are evaluated to determine the effectiveness of repopulation with stem cells.

The flow regimes and timing for partial decellularization may be varied in the according to different embodiments of the present subject matter. Likewise, the level of decellularization in a given embodiment is selected to be most appropriate for the exact distribution of the cells expected. To this end, various mathematical modeling of flow and transport in the lung may be applied.

Turning to FIG. 10, a lung perfusion apparatus 1000 is provided. The lungs 1001 are perfused using a clinical perfusion setup 1002, with the flow loops shown in FIG. 9A-B. Following cell seeding and 7 days of perfusion with culture medium through the airway, with perfusion of vasculature with PERFADEX® solution, the lungs are switched to ventilation and evaluated using the ELVP system 1000. Both flow regimes are optimized with the aid of flow modeling.

Figure 11:
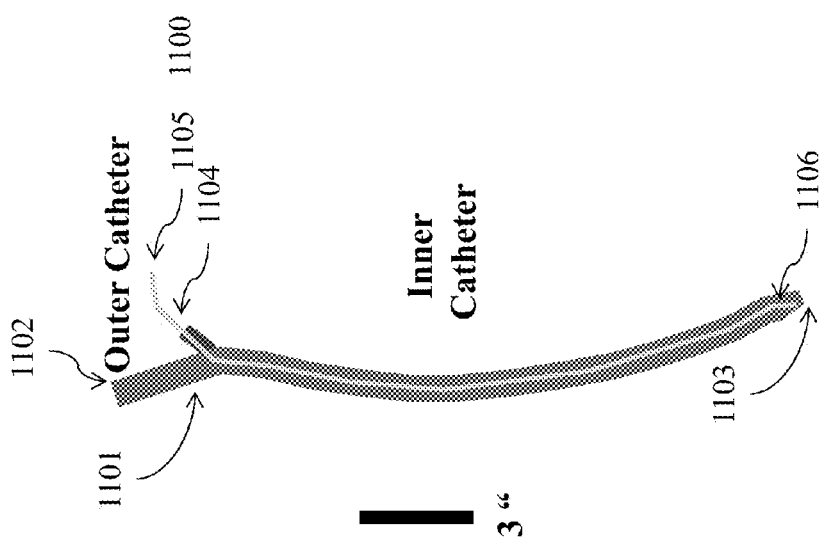
FIG. 11 is a schematic representation of a device in accordance with an embodiment of the present disclosure.

Referring to FIG. 11, and in accordance with another aspect, a device having a variety of clinical applications in acute (ARDS) and chronic lung injury, lung cancer, and transplant diagnostics as well as routine pulmonary toilet therapy is provided. In one embodiment, the device 1100 includes an outer tubular member 1101 having a longitudinal axis disposed between a proximal end 1102 and a distal end 1103, and an inner tubular member 1104 coaxially disposed within the outer tubular member 1101. The inner tubular member 1104 has a longitudinal axis between a proximal end 1105 and a distal end 1106. The distal end 1103 of the outer tubular member 1101 includes a plurality of openings to permit fluid communication between the outer and inner tubular members. In one embodiment, the proximal end 1102 of the outer tubular member 1101 includes a luer. The distal end 1103 of the outer member can include a tip region, such as a tapered or chamfered tip. In some embodiments, the tip can be composed of material having a softer durometer than the remainder of the outer tubular member. The inner tubular member 1104 can have distal end including a reverse taper.

The plurality of openings may include a circular, oval or oblong shape. In some embodiments, the longest distance from end to end of the shape is less than about ½ inch, preferably less than about ¼ inch or about ⅛ inch.

The outer tubular member is adapted to remove decellularization reagents introduced by the inner tubular member. The inner tubular member is adapted to introduce decellularization reagents to a lung. The device may further include an ultrasound transducer to facilitate the removal of secretions and/or cells with agitation.

Figure 12:
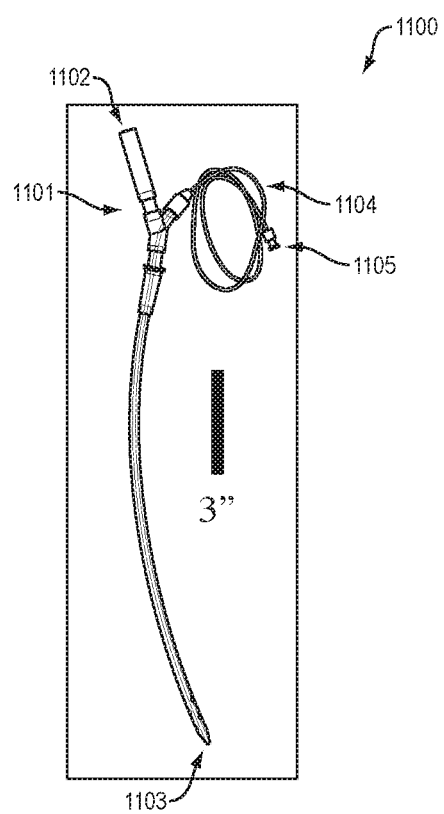
FIG. 12 depicts a device according to an embodiment of the present disclosure.

An alternative view of device 1100 is provided in FIG. 12.

Figure 13:
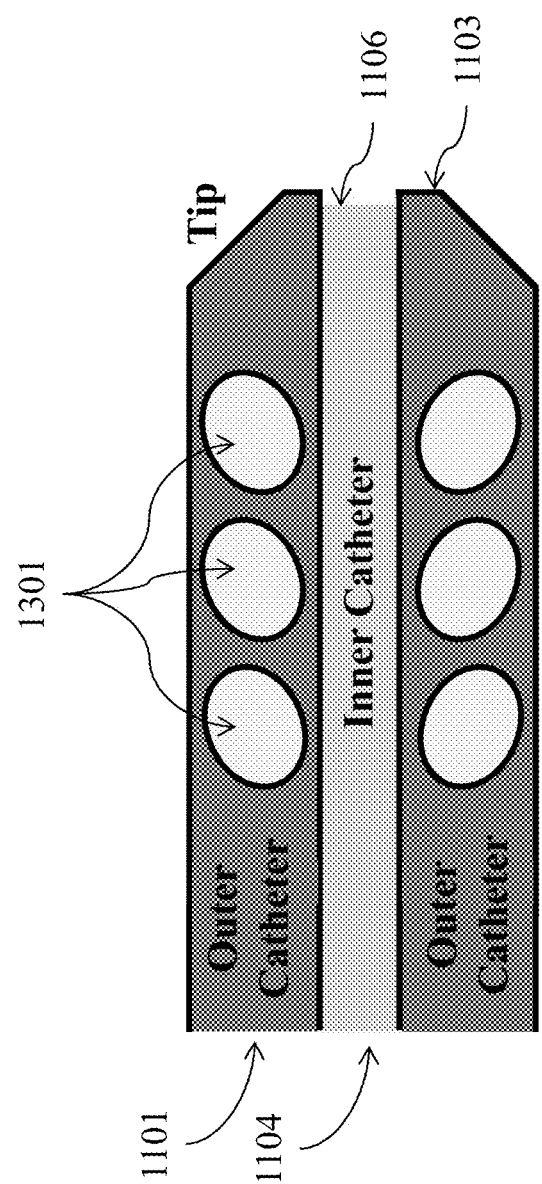
FIG. 13 depicts a schematic of inner catheter, outer catheter and tip of the device of FIG. 11.

As best seen in FIG. 13, the outer tubular member 1101 includes a plurality of openings 1301 at the distal section of the member. The inner member 1104 is coaxially disposed within the outer member 1101.

Figure 14:
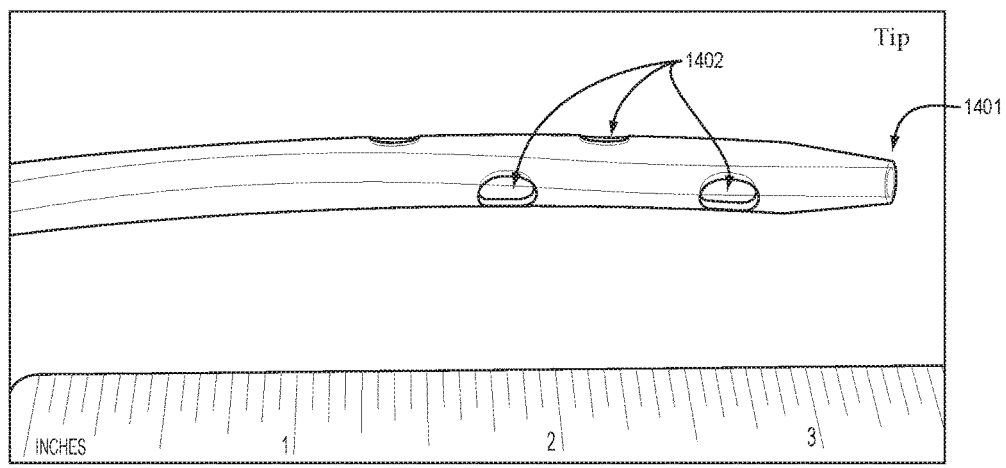
FIG. 14 depicts an embodiment of the tip of the device according to an embodiment of the present disclosure.

As shown in FIG. 14, the device may include a distal tip 1401. The distal tip 1401 can be downwardly tapering to a distal end. The plurality of openings 1402 are disposed proximal to the distal end and taper.

Figure 15:
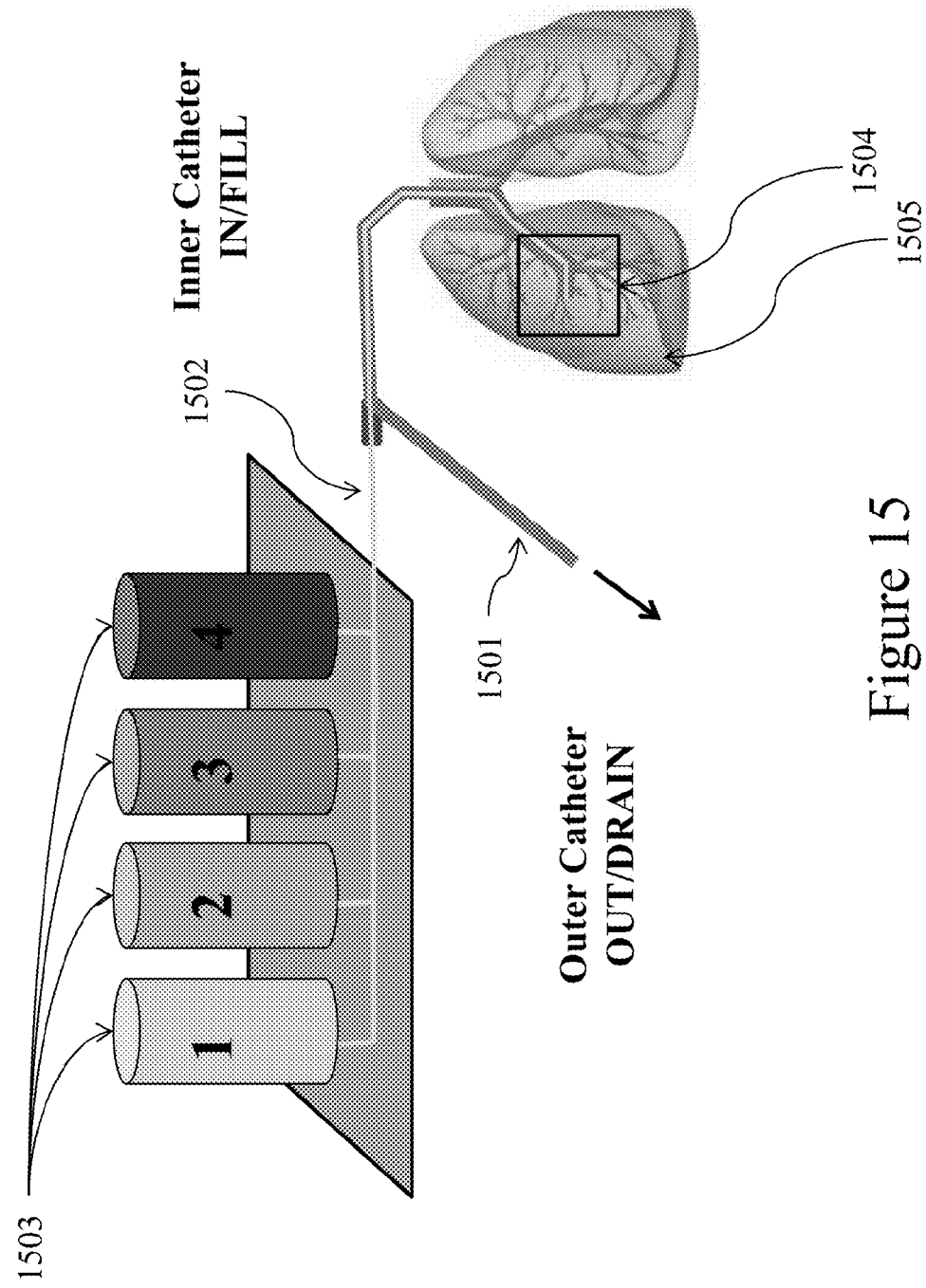
FIG. 15 depicts a system in accordance with an embodiment of the present disclosure.

As shown in FIG. 15, in another aspect a system is provided suitable for lung decellularization or lavage. The system includes an outer tubular member 1501 having a longitudinal axis disposed between a proximal end and a distal end, and an inner tubular member 1502 coaxially disposed within the outer tubular member having a longitudinal axis between a proximal end and a distal end, wherein the distal end of the outer tubular member includes a plurality of openings to permit fluid communication between the outer and inner tubular members, wherein the device is operatively connected to one or more containers 1503 comprising lavage or decell solution. The system may further comprise a pump to pump the lavage or decell solution into the device. The lavage or decell solution is pumped into the inner tubular member of the device.

Figure 16:
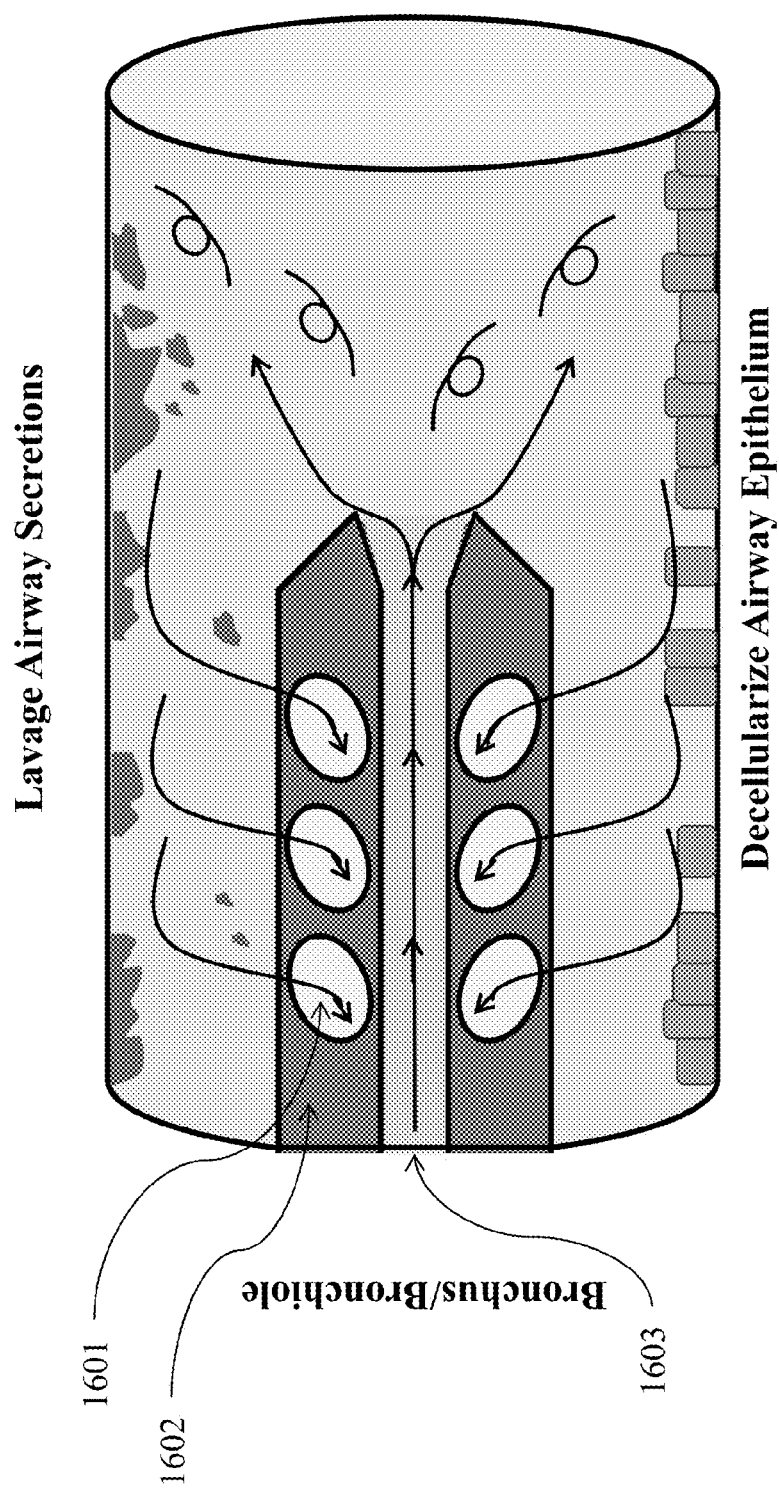
FIG. 16 depicts a schematic representation of the device in use in accordance with the present disclosure.

FIG. 16 provides a detail view of region 1504 of lung 1505 with a deployed system according to the present disclosure. In use, as illustrated in FIG. 16, cellular fluid enters the plurality of openings 1601 and traverse the outer tubular member 1602, and the inner tubular member 1603 introduces fluid such as decellularization fluid into the lung.

Figure 17:
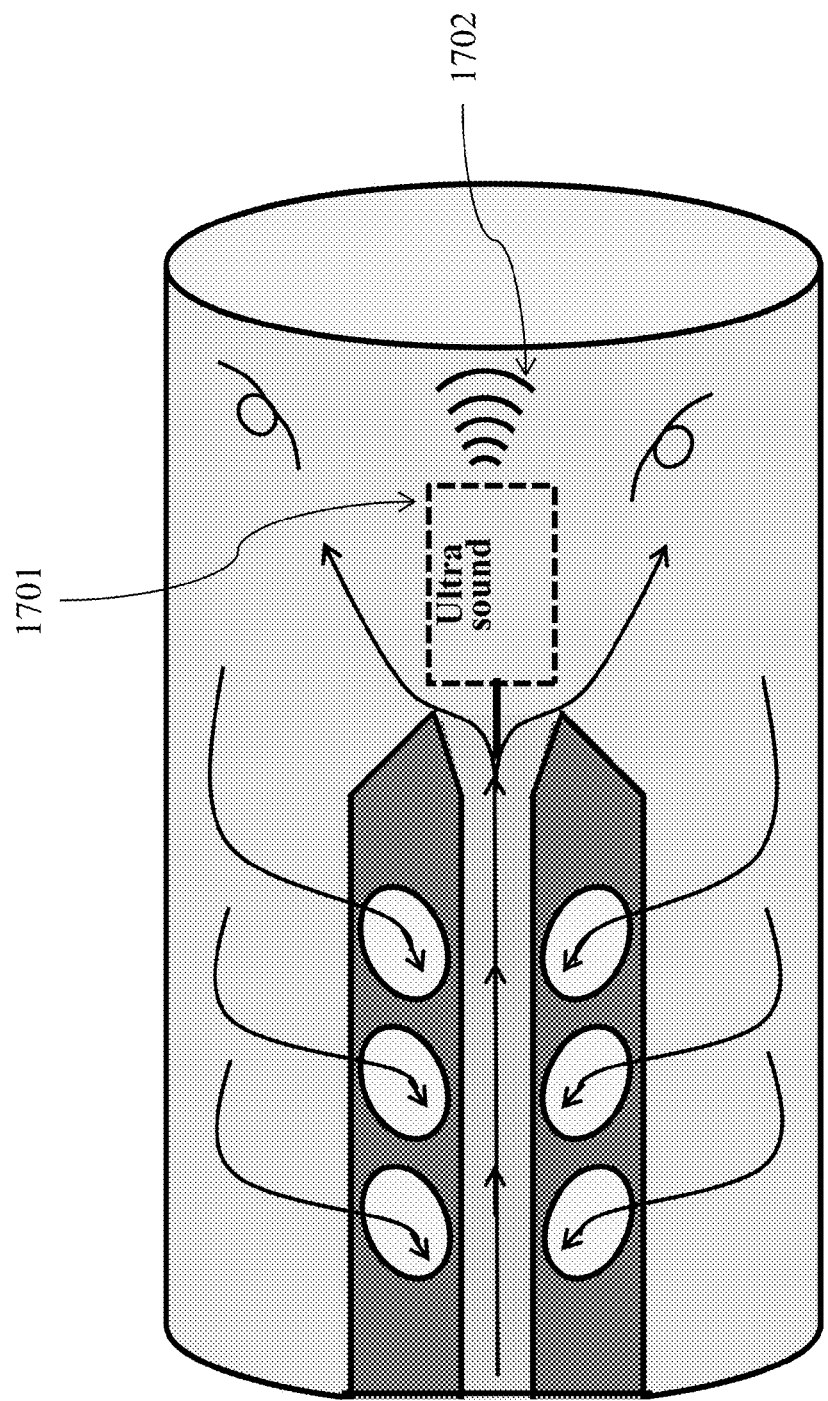
FIG. 17 depicts another embodiment of a device of the present disclosure having an ultrasound transducer.

Referring to FIG. 17, some embodiments include an ultrasound transducer 1701 to facilitate agitation. Transducer 1701 emits sound waves 1702, which are configured to agitate the surrounding fluid.

While the disclosed subject matter is described herein in terms of certain exemplary embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A device adapted for insertion into the bronchus of a lung via the airway, for treatment or removal of cells from the lung, the device comprising:
   an outer tubular member having a longitudinal axis disposed between a proximal end and a distal end,
   an inner tubular member having a longitudinal axis between a proximal end and a distal end,
   wherein only a portion of the inner tubular member is coaxially disposed within the outer tubular member, further wherein the distal end of the outer tubular member includes a plurality of openings to permit fluid communication between the outer and inner tubular members, and the proximal end of the inner tubular member is in fluid communication with decellularization reagent.

2. The device of claim 1, wherein the proximal end of the outer tubular member includes a luer.

3. The device of claim 1, wherein the distal end of the outer member includes a tip region.

4. The device of claim 3, wherein the tip region is tapered.

5. The device of claim 1, wherein the inner tubular member has a distal end including a reverse taper.

6. The device of claim 1, wherein the plurality of openings includes oblong shaped openings having a length less than about ¼ inch.

7. The device of claim 1, wherein the outer tubular member is adapted to remove decellularization reagents introduced by the inner tubular member.

8. The device of claim 1, wherein the inner tubular member is operatively connected to a pump to control fluid communication to the decellularization reagents.

9. The device of claim 1, wherein the device further includes an ultrasound transducer.

10. A system adapted for insertion into the bronchus of a lung via the airway, the system comprising: an outer tubular member having a longitudinal axis disposed between a proximal end and a distal end; and an inner tubular member coaxially disposed within a portion of the outer tubular member having a longitudinal axis between a proximal end and a distal end, wherein the distal end of the outer tubular member includes a plurality of openings to permit fluid communication between the outer and inner tubular members, wherein the inner tubular member is operatively connected to one or more containers comprising lavage or decell solution.

11. The system of claim 10, wherein the system further comprises a pump to pump the lavage or decell solution into the device.

12. The system of claim 11, wherein the lavage or decell solution is pumped into the inner tubular member of the device.

13. The system of claim 10, wherein at least one of the inner or outer tubular members includes an ultrasound transducer.

14. A medical apparatus comprising:
a first tubular member adapted for insertion in the bronchus of a lung;
a second tubular member adapted for insertion in the pulmonary artery of the lung;
a first fluid reservoir in fluid communication with a first pump and with the first tubular member, a first fluid of the first fluid reservoir circulating through the first tubular member by the first pump, wherein the first fluid is decellularization reagent; and
a second fluid reservoir in fluid communication with a second pump and with the second tubular member, a second fluid of the second fluid reservoir circulating through the second tubular member by the second pump;
wherein the first tubular member comprises:
an outer tubular member having a longitudinal axis disposed between a proximal end and a distal end,
an inner tubular member having a longitudinal axis between a proximal end and a distal end,
wherein only a portion of the inner tubular member is coaxially disposed within the outer tubular member, further wherein the distal end of the outer tubular member includes a plurality of openings to permit fluid communication between the outer and inner tubular members, and the proximal end of the inner tubular member is in fluid communication with the decellularization reagent of the first fluid reservoir.

15. The apparatus of claim 14 wherein the second fluid comprises a solution comprising about 5% dextran with Mw of about 40,000, $Na^+$ 138 mmol, $K^+$ 6 mmol, $Mg\ 2^+$ 0.8 mmol, $Cl^-$ 142 mmol, $SO_4^{2-}$ 0.8 mmol, $H_2PO_4^-$ plus $HPO_4^{2-}$ 0.8 mmol and glucose 5 mmol per 1,000 ml.

16. The apparatus of claim 15 wherein the decellularization reagent is CHAPS solution.

* * * * *